United States Patent
Kondou et al.

(10) Patent No.: US 6,596,349 B2
(45) Date of Patent: Jul. 22, 2003

(54) TERPHENYL DERIVATIVE, LIQUID CRYSTAL COMPOSITION AND LIQUID CRYSTAL DISPLAY DEVICE

(75) Inventors: Tomoyuki Kondou, Ichihara (JP); Shuichi Matsui, Ichihara (JP); Kazutoshi Miyazawa, Ichihara (JP); Hiroyuki Takeuchi, Ichihara (JP); Yasuhiro Kubo, Ichihara (JP); Fusayuki Takeshita, Kimitsu (JP); Etsuo Nakagawa, Ichihara (JP)

(73) Assignee: Chisso Corp., Osaka (JP)

( * ) Notice: Subject to any disclaimer, the term of this patent is extended or adjusted under 35 U.S.C. 154(b) by 0 days.

(21) Appl. No.: 09/836,315

(22) Filed: Apr. 18, 2001

(65) Prior Publication Data

US 2001/0038891 A1 Nov. 8, 2001

Related U.S. Application Data

(62) Division of application No. 09/269,287, filed on Mar. 25, 1999, now Pat. No. 6,344,247.

(30) Foreign Application Priority Data

Sep. 25, 1996 (JP) .............................. 8-272856

(51) Int. Cl.⁷ ..................... C09K 19/12; C07C 25/13; C07C 43/225
(52) U.S. Cl. ................... 428/1.1; 252/299.66; 570/127; 570/129; 567/661
(58) Field of Search .................. 428/1.1; 252/299.66, 252/299.01; 570/129, 127; 568/656, 661

(56) References Cited

U.S. PATENT DOCUMENTS

| | | | |
|---|---|---|---|
| 5,328,644 A | * 7/1994 | Goulding et al. ...... | 252/299.66 |
| 5,422,035 A | 6/1995 | Bartmann et al. | |
| 5,498,365 A | * 3/1996 | Nolan et al. .......... | 252/299.01 |
| 5,626,793 A | 5/1997 | Reiffenrath et al. | |
| 5,718,840 A | 2/1998 | Plach et al. | |
| 5,762,828 A | 6/1998 | Tanaka et al. | |
| 5,871,665 A | 2/1999 | Coates et al. | |
| 5,932,138 A | 8/1999 | Plach et al. | |
| 5,948,319 A | 9/1999 | Tanaka et al. | |
| 6,004,479 A | 12/1999 | Weber et al. | |
| 6,180,026 B1 | * 1/2001 | Rieger et al. .......... | 252/299.63 |
| 6,344,247 B1 | * 2/2002 | Kondou et al. ............... | 428/1.1 |

* cited by examiner

Primary Examiner—Shean C. Wu
(74) Attorney, Agent, or Firm—Browdy and Neimark PLLC

(57) ABSTRACT

The present invention provides liquid crystalline compounds having a high voltage holding ratio and a low threshold voltage, little variation of these properties with temperature change, high Δn, and good compatibility with other liquid crystal materials particularly under a low temperature; liquid crystal compositions containing these crystalline compounds; and liquid crystal display devices made using these liquid crystal compositions. The liquid crystalline compounds are terphenyl derivatives represented by general formula (1):

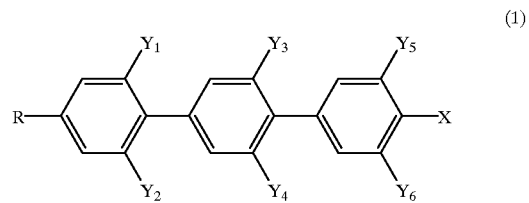

(1)

wherein R represents a straight or branched alkyl group of 1–20 carbon atoms, and any methylene groups ($-CH_2-$) not adjacent each other in each alkyl group may be replaced by oxygen atoms; X is a halogen atom, $-OCF_3$, $-OCF_2H$, $-CF_3$, $-CF_2H$ or $-CFH_2$; $Y_1$, $Y_2$, $Y_3$, $Y_4$, $Y_5$ and $Y_6$ independently represents H or F, but at least two of $Y_1$, $Y_2$, $Y_3$ and $Y_4$ represent F; and any atom constituting these compounds may be substituted by its isotope.

16 Claims, No Drawings

TERPHENYL DERIVATIVE, LIQUID CRYSTAL COMPOSITION AND LIQUID CRYSTAL DISPLAY DEVICE

CROSS REFERENCE TO RELATED APPLICATIONS

The present application is a divisional of Ser. No. 09/269,287, filed Mar. 25, 1999, now U.S. Pat. No. 6,344,247 the entire contents of which are hereby incorporated by reference.

FIELD OF THE INVENTION

The present invention relates to new liquid crystalline compounds and liquid crystal compositions. More particularly, the present invention relates to terphenyl derivatives having a fluorine-substituted-1,4-phenylene group, liquid crystal compositions containing them, and liquid crystal display devices made using the liquid crystal compositions.

BACKGROUND OF THE INVENTION

Liquid crystal display devices using liquid crystalline compounds (in this description, the term "liquid crystalline compound" is used as a generic term for a compound exhibiting a liquid crystal phase or a compound not exhibiting a liquid crystal phase but useful as a constituent of a liquid crystal composition) are widely used in displays of clocks, watches, electronic calculators, word processors and the like. Lately, much research has been conducted for a TFT type display having characteristics such as a high contrast and a broad visual field angle.

Liquid crystal compositions for TFT need physical properties, such as a high voltage holding ratio, low threshold voltage (Vth), little variation of these properties with temperature, broad temperature range of liquid crystal layers, excellent compatibility with other liquid crystal materials and low viscosity. Further, the compositions having a high optical anisotropy ($\Delta n$) are useful for improving the response speed.

For these reasons, as a component of liquid crystalline compounds having such characteristics, fluorine-substituted liquid crystalline compounds are preferably used, as described in (1) Japanese Patent Publication 63-13411, (2) Japanese Patent Publication 63-44132, (3) Japanese Patent Laid-open 2-233626, (4) Japanese Patent Laid-open 2-501311, (5) Japanese Patent Laid-open 3-500413, (6) Japanese Patent Laid-open 3-504018, (7) Japanese Patent Laid-open 5-502676, (8) Japanese Patent Laid-open 6-504032, (9) GB2257701 and (10) EP439089, many synthesis methods and researches have been done.

SUMMARY OF THE INVENTION

It is an object of the present invention to provide liquid crystalline compounds having a very little variation of these properties with temperature change, high $\Delta n$, and good compatibility with other liquid crystal materials particularly at low temperatures, liquid crystal compositions containing these compounds, and liquid crystal display devices made using the liquid crystal compositions.

The present inventors have earnestly studied to resolve the above problems and have completed the studies by obtaining the merphenyl derivatives having the above properties. The compounds are represented by general formula (1);

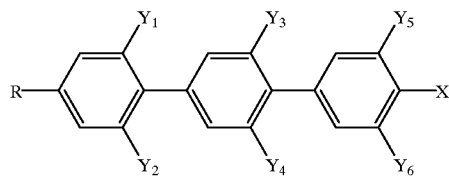

wherein R represents a straight or branched alkyl group of 1–20 carbon atoms, and any methylene groups ($-CH_2-$) not adjacent each other in each alkyl group may be replaced by oxygen atoms; X shows an halogen atom, $-OCF_3$, $-OCF_2H$, $-CF_3$, $-CF_2H$ or $-CFH_2$; $Y_1$, $Y_2$, $Y_3$, $Y_4$, $Y_5$ and $Y_6$ independently represents H or F, but at least two of $Y_1$, $Y_2$, $Y_3$ and $Y_4$ represent F;

in which a) in case of $Y_1=Y_2=Y_3=Y_4=H$ and $X=F$, $Y_5=Y_6=F$, b) in case of $Y_1=Y_2=F$, $Y_3=Y_4=H$ and $X=-CF_3$ or $-CF_2H$, $Y_5=Y_6=F$ or $Y_5=Y_6=H$, c) in case of $Y_1=Y_3=F$, $Y_2=Y_4=H$ and $X=-CF_3$, $Y_5=Y_6=F$, d) in case of $Y_1=Y_3=F$, $Y_2=Y_4=H$ and $X=-OCF_3$, $Y_5=F$, e) in case of $Y_3=Y_4=F$, $Y_1=Y_2=H$ and $X=F$, $Y_5=Y_6=F$, f) in case of $Y_3=Y_4=F$, $Y_1=Y_2=H$ and $X=-OCF_3$ or $-CF_3$, $Y_5=F$, g) in case of $Y_1=Y_2=Y_3=F$, $Y_4=H$ and $X=CL$, $Y_5=Y_6=F$, h) in case of $Y_1=Y_2=Y_3=F$, $Y_4=H$ and $X=F$, $-CF_3$ or $-CF_2H$, $Y_5=F$, and i) in case of $Y_1=Y_2=Y_3=Y_4=F$ and $X=Cl$ or $-OCF_3$, $Y_5=F$, however, in case of $Y_1=Y_2=F$ and $Y_3=Y_4=H$, in case of $Y_1=Y_3=F$ and $Y_2=Y_4=H$, and in case of $Y_3=Y_4=F$ and $Y_1=Y_2=H$, not $X=Cl$, and any atom in the compound may be replaced by an isotope thereof.

A part of the compounds represented by general formula (1) are formally included in the compounds described in the above references (6) to (10). However, in these references, there is no description of data such as values of physical properties of the compounds of the present invention, and definite or embodied characteristics of these compounds, so that the present invention is not suggested.

The compounds represented by general formula (1) and be classified as follows into (a-1) to (a-6).

  (a-1)

  (a-2)

  (a-3)

  (a-4)

  (a-5)

  (a-6)

In the formula, R represents as the same meaning as described above, B represents a 1,4-phenylene group, B(F) represents a 3-fluoro-1,4-phenylene, B(F,F) represents a 3,5-difluoro-1,4-phenylene group, and Q represents the following group:

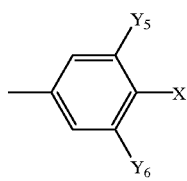

wherein $Y_5$, $Y_6$ and F represent as the same meaning as described above.

As described above, in the formula, R represents a straight or branched alkyl group of 1–20 carbon atoms. As a straight alkyl group, methyl, ethyl, propyl, butyl, pentyl, hexyl, heptyl, decyl, pentadecyl or eicosyl can be exemplified. As a branched alky group, isopropyl, secbutyl, tert-butyl, 2-methyl-butyl, isopentyl, isohexyl, 3-ethyloctyl, 3,8-dimethyltetradecyl or 5-ethyl-5-methylnonadecyl can be exemplified. Further, the branched alkyl group may be optionally active group, and compounds having such a group are useful as chiral doping agents.

Any methylene groups not adjacent each other in the alkyl groups may be replaced by oxygen atoms, and alkoxy groups such as methoxy, ethoxy, propoxy, butoxy, pentyloxy and nonyloxy, and alkoxyalkyl groups such as methoxymethyl, methoxyethyl, methoxypropyl, methoxybutyl, methoxypentyl, methoxyoctyl, ethoxymethyl, ethoxyethyl, ethoxypropyl, ethoxyhexyl, propoxymethyl, propoxyethyl, propoxypropyl, propoxypentyl, butoxymethyl, butoxyethyl, butoxybutyl, pentyloxymethyl, pentyloxybutyl, hexyloxymethyl, hexyloxyethyl, hexyloxypropyl, heptyloxymethyl and octyloxymethyl are examples thereof.

DETAILED DESCRIPTION OF THE INVENTION

Although the liquid crystalline compounds of the present invention represented by general formula (1) may be prepared by a method of common organic synthesis, as an example, the compounds may be easily prepared by the following method.

scheme 1

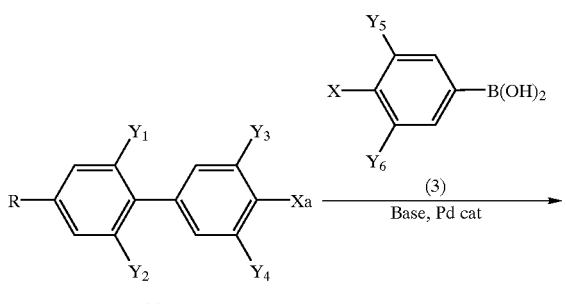

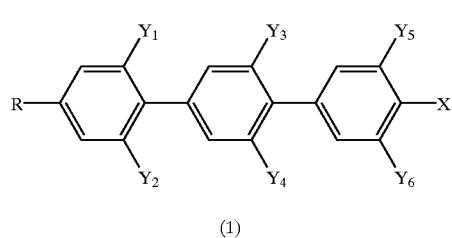

scheme 2

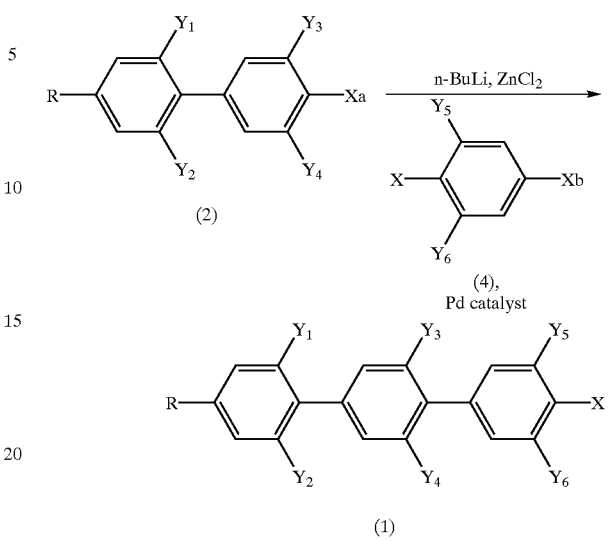

wherein R, $Y_1$–$Y_6$ and X have the same meaning as described above, Xa and Xb are halogen atoms.

Namely, as shown in scheme 1, in mixed solvent of three ingredients; toluene, xylene or the like, alcohol such as ethanol, and water; halogen compound (2) and dihydroxyborane derivative (3) can be reacted in the presence of a base such as $K_2CO_3$ or $Na_2CO_3$ and a catalyst such as carbon-carried palladium (Pd—C), $Pd(PPh_3)_4$ or $PdCl_2(PPh_3)_2$ to produce compound (1) of the present invention. Further, as shown in scheme 2, after reacting halogen compound (2) with a lithium compound such as n-BuLi or sec-BuLi and a zinc compound such as $ZnCl_2$ or $ZnBr_2$, the reactant may be reached with halogen compound (4) to obtain the above compound (1).

To introduce substituent X in to the benzene ring, a raw material, in which X has been previously introduced can be used, or, X can be easily introduced by a well-known reaction at any step. Embodied examples are shown in the following. (In the following formulas, Rx shows the following group).

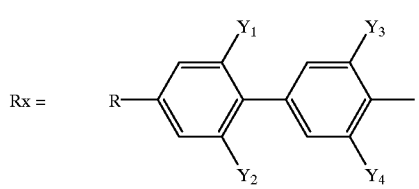

wherein R, and $Y_1$–$Y_4$ show the same meaning as described above.

scheme 3

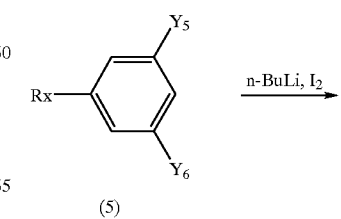

wherein $Y_5$ and $Y_6$ have the same meaning as described above.

Namely, as shown in scheme 3, compound (5) and a lithium compound such as n-butyllithium and iodine are reacted to obtain compound (6). Compound (6) and sodim trifluoroacetate/copper iodine (I) (G. E. Carr et al., Journal of the Chemical Society Perkin Trans Actions I, 921 (1988)) or methyl fluorosulfonyldifluoro acetate/copper iodide (I) (Q. Y. Chen et al., Journal of the Chemical Society Chemical Communications, 705 (1989)) can be reacted to obtain trifluoromethyl compound (7).

As shown in scheme 4, compound (5), a lithium compound such as n-butyllithium, and a formylation agent such as N-formylpiperidine (G. A. Olah et al., Angewandte Chemie International Edition in English, 20, 878 (1981)), N-formylmorpholine (G. A. Olah et al., The Journal of Organic Chemistry, 49, 385 (1984)) or dimethylformamide (DMF) (G. Boss et al., Chemich Berichte, 1199 (1989)) can be reacted to obtain compound (8), and the reactant can be reached with a fluorinating agent such as diethylamino sulfur trifluoride (DAST) (W. J. Middleton et al., The Journal of Organic Chemistry, 40, 574 (1975), S. Rozen et al., Tetrahedron Letters, 41, 111 (1985), M. Hudlicky, Organic Reactions, 35, 513 (1988), P. A. Messina et al., Journal of Fluorine Chemistry, 42, 137 (1989)), or morpholino sulfur trifluoride (K. C. Mange et al., The Journal of Fluorine Chemistry, 43, 405 (1989) to obtain difluoromethyl compound (9).

As shown in scheme 5, after reducing compound (8) with a reducing agent such as sodium borohydride (SBH), lithium aluminum hydride (LAH), diisobutylaluminum hydride (DIBAL) or sodium bis(2-methoxyethoxy) aluminum (SBMEA) to obtain compound (10), the compound (10) can be reacted with a fluorinating agent such as DAST to produce monofluoromethyl compound (11).

As shown in scheme 6, compound (12) is changed to xanthate (13) by a method such as Albert et al. (Synthetic Communication, 19 547 (1989)). The resulting compound can be fluorinated by a method of Kurohoshi et al.

(Tetrahedron Letters, 33, 29, 4173 (1992)) to produce trifluoromethoxy compound (14).

In addition, as shown in scheme 7, compound (12) is fluorinated is a system of chlorodifluoromethane/sodium hydroxide (Japanese Patent Laid-open 3-500413) to produce difluoromethoxy compound (15). Otherwise, it can be produced by a method of Chen et al. (The Journal of Fluorine Chemistry, 44, 433 (1989)).

The halogen compound and dihydroxyborane derivative, which are raw materials, can be produced by a well-known method of common organic synthesis, for example, a simple method as shown in the following.

scheme 8

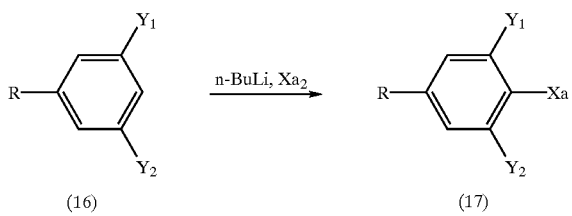

(16)        (17)

scheme 9

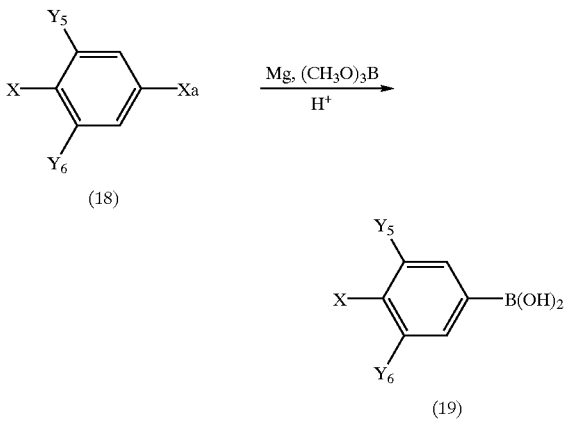

(18)

(19)

wherein R, X, Xa, $Y_1$, $Y_2$, $Y_5$ and $Y_6$ show the same meaning as described above.

Namely, as shown in scheme 8, by reacting compound (16) with a lithium compound such as n-BuLi and iodine or bromine, halogen compound (7) can be produced.

As shown in scheme 9, by the reaction a grignard reagent prepared from halogen compound (18) and magnesium, with a borane derivative such as trimethoxyborane or triisopropyloxyborane, and then by hydrolysis with hydrochloride or the like, dihydroxyborane derivative (19) can be produced.

The compound, not shown in the schemes, having —O— in group R of general formula (1) can be produced by reacting a halogen compound and alcohol or phenol in a solvent such as dimehylsulfoxide, DMF, 1,2-dimethoxyethane, tetrahydrofurane, hexamethylphosphric acid triamide or toluene in the presence of a base such as sodium amide (J. B. Right et al., Journal of the American Chemical Society, 70, 3098 (1948)), potassium carbonate (W. T. Olson et al., Journal of the American Chemical Society, 69, 2451 (1947)), triethylamine (R. L. Merker et al., The Journal of Organic Chemistry, 26, 5180 (1961)), sodium hydoxide (C. Wilkins, Synthesis, 156 (1973)), potassium hydroxide (J. Rebek et al., The Journal of Organic Chemistry, 44, 1485 (1979)), barium hydroxide (Kawabe et al., The Journal of Organic Chemistry, 37, 4210 (1972)) and sodium hydride (C. J. Stark, Tetrahedron Letters, 22, 2089 (1981), K. Takai et al. Tetrahedron Letters, 21, 1657 (1980)).

The above reactions are well-known, and if necessary, the other known reactions can also be used.

The liquid crystalline compounds of the present invention obtained thus have a very high voltage holding ratio, a low threshold voltage, very little variation of these properties with temperature and high Δn, and these compounds can be easily mixed with various liquid crystal materials and have good solubility at a low temperature.

In addition, the liquid crystalline compounds of the present invention are physically and chemically very stable under common conditions when the compounds are used for liquid crystal display devices, and are very excellent as a constituent of nematic liquid crystal compositions.

The compounds of the present invention can be preferably used as a constituent of liquid crystal compositions for TN, STN and TFT.

The liquid crystal compositions of the present invention preferably contain at least one compound represented by general formula (1) at a ratio of 0.1–99.9% by weight to develop excellent characteristic.

More particularly, the liquid crystal compositions provided by the present invention are finally obtained by mixing at least one compound represented by general formula (1) as a first component with the compounds selected from the group comprising of compounds represented by general formulae (2)–(9) according to the purpose of the liquid crystal composition.

As preferably embodied compounds represented by general formulae (2)–(4) are used in the liquid crystal compositions of the present invention, the following compounds are exemplified.

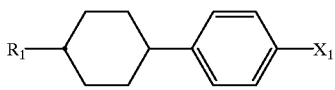

(2-1)

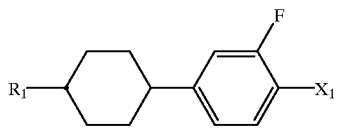

(2-2)

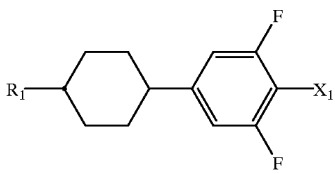

(2-3)

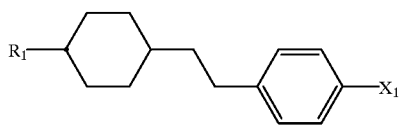

(2-4)

-continued
(2-5) 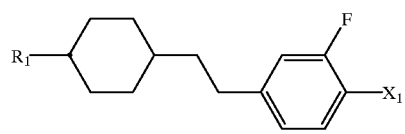
(2-6) 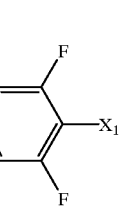
(2-7) 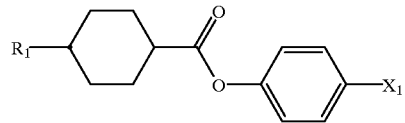
(2-8) 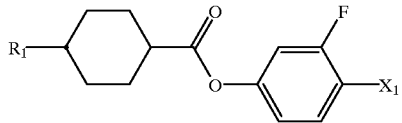
(2-9) 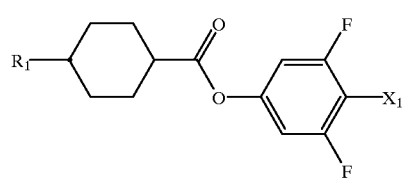
(3-1) 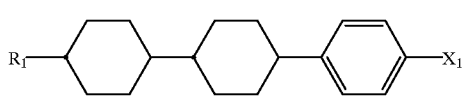
(3-2) 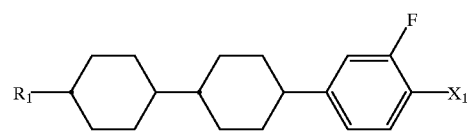
(3-3) 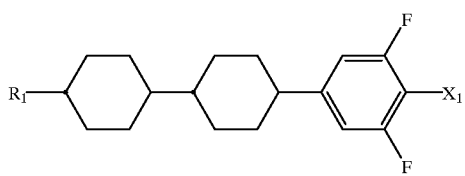
(3-4) 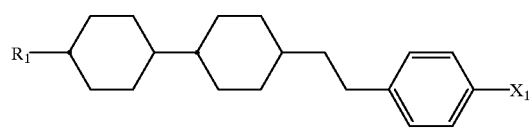
(3-5) 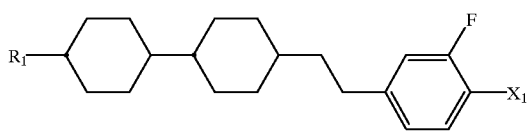
(3-6) 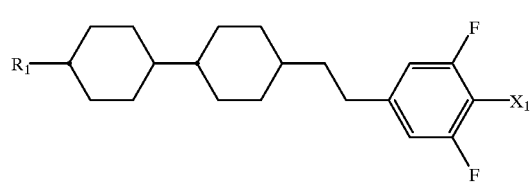
(3-7) 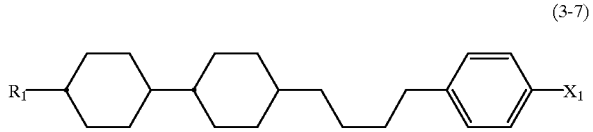
(3-8) 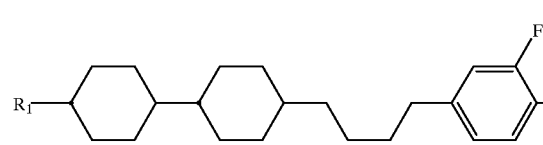
(3-9) 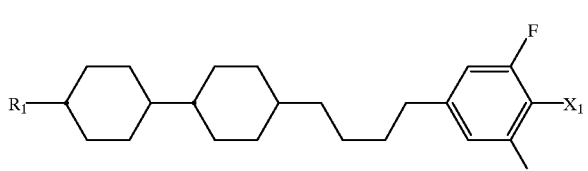
(3-10) 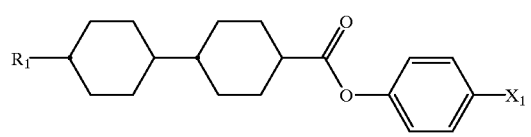
(3-11) 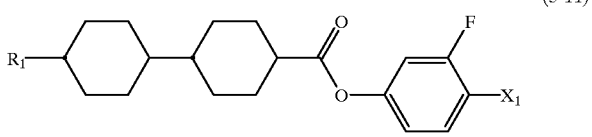
(3-12) 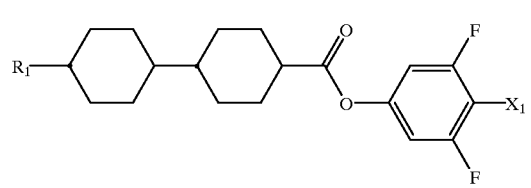
(3-13)

-continued
(3-14)
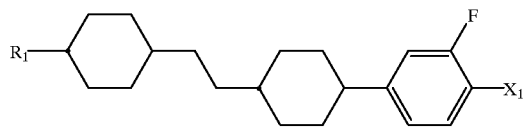
(3-15)
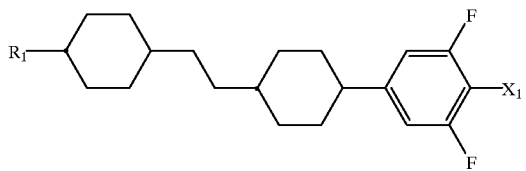
(3-16)
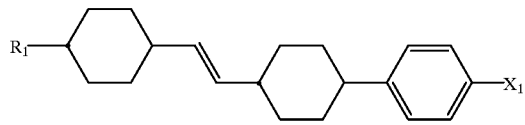
(3-17)
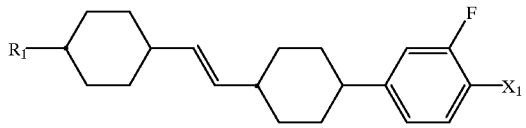
(3-18)
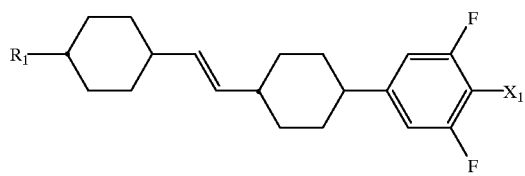
(3-19)
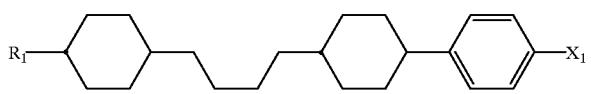
(3-20)
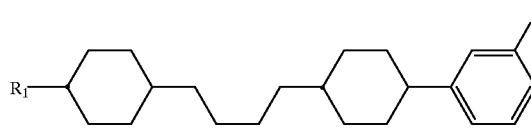
(3-21)
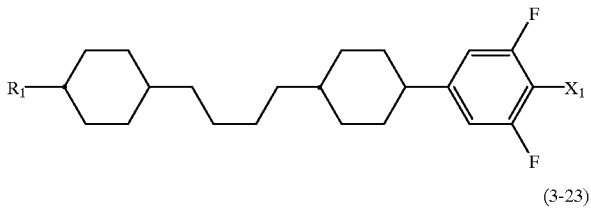
(3-22)
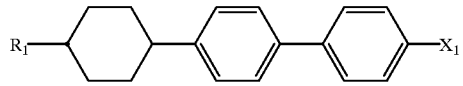
(3-23)
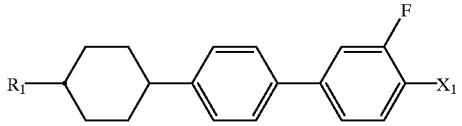
(3-24)
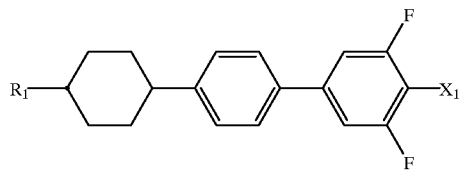
(3-25)
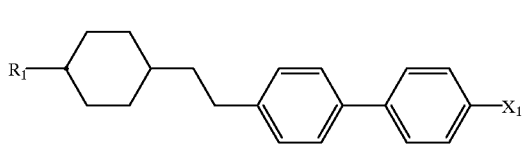
(3-26)
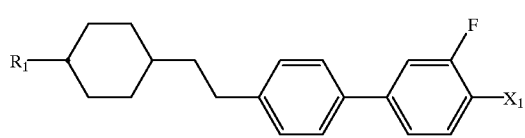
(3-27)
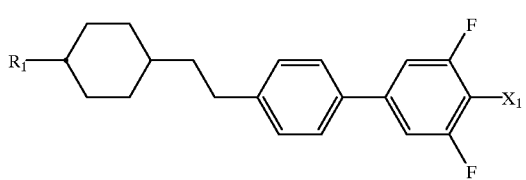
(3-28)
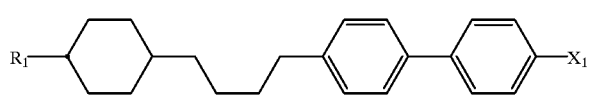
(3-29)
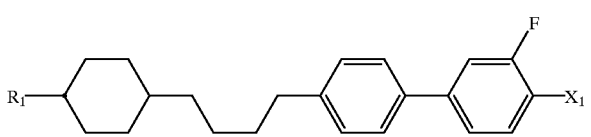

-continued
(3-30)
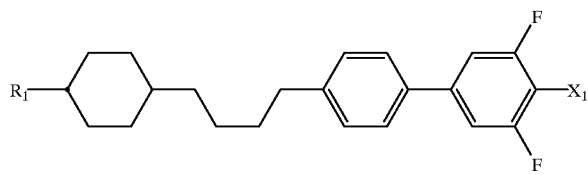
(3-31)
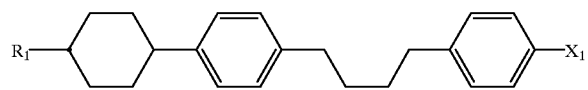
(3-32)
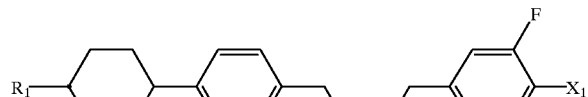
(3-33)
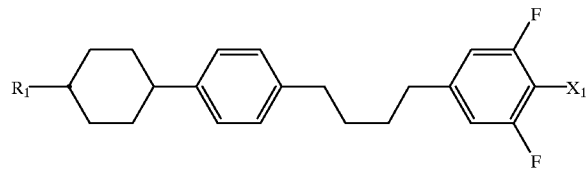
(3-34)
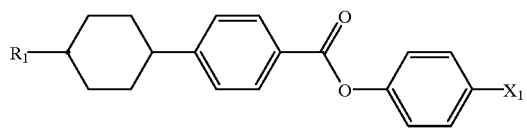
(3-35)
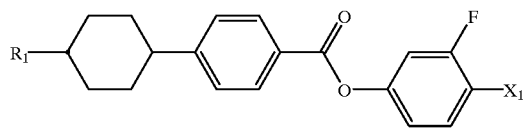
(3-36)
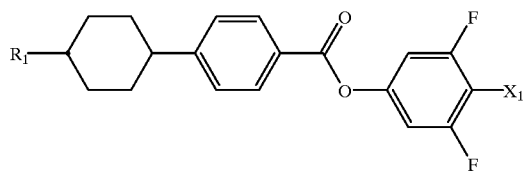
(3-37)
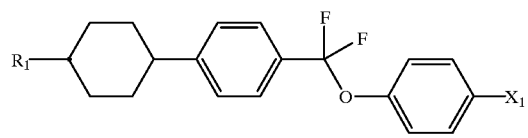
(3-38)
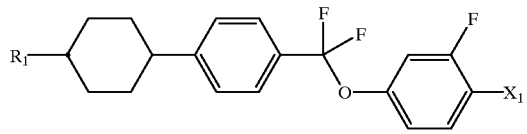
(3-39)
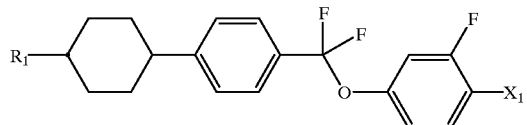
(3-40)
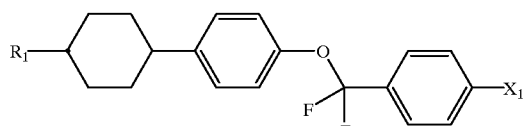
(3-41)
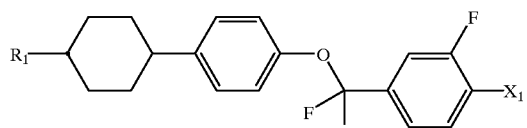
(3-42)
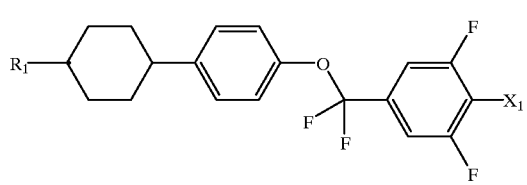
(3-43)
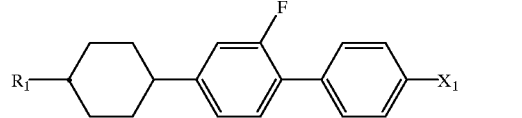
(3-44)
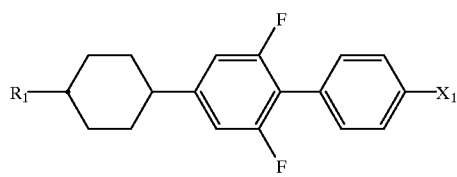
(3-45)
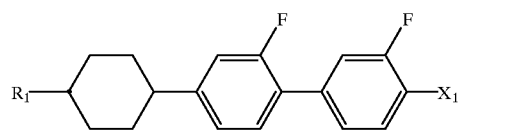

-continued
(3-46) 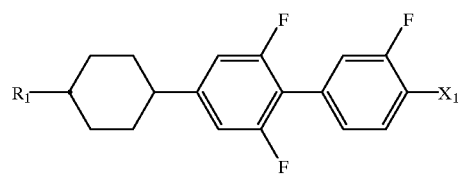
(3-47) 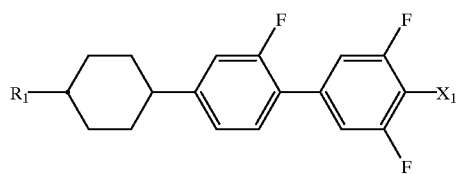
(3-48) 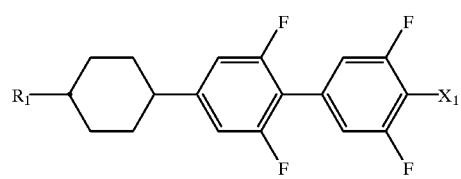
(3-49) 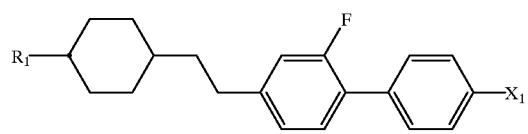
(3-50) 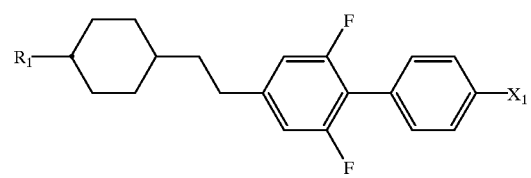
(3-51) 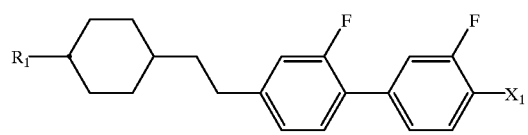
(3-52) 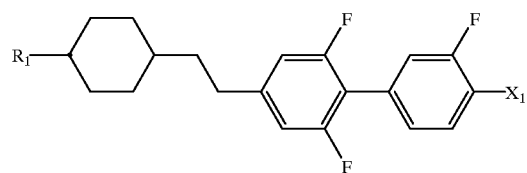
(3-53) 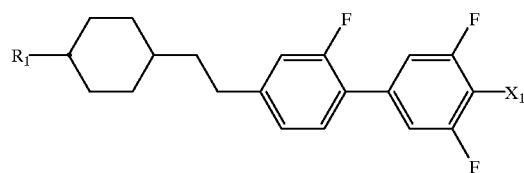
(3-54) 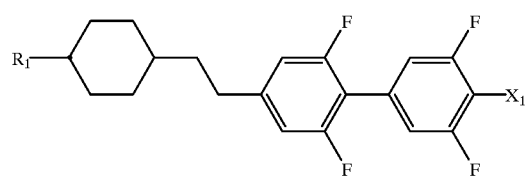
(3-55) 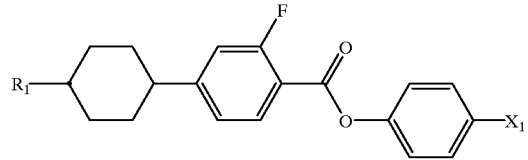
(3-56) 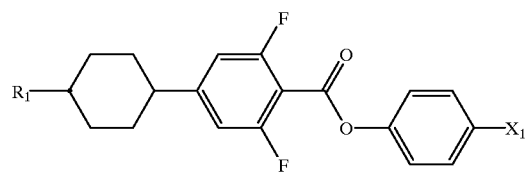
(3-57) 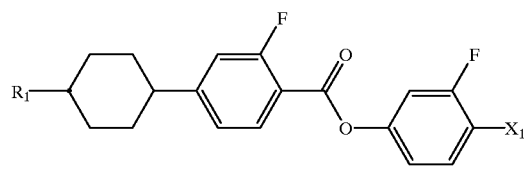
(3-58) 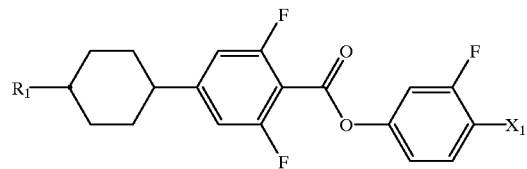
(3-59) 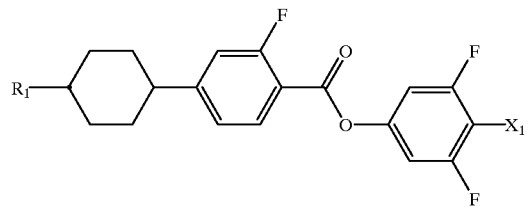

-continued
(3-61)
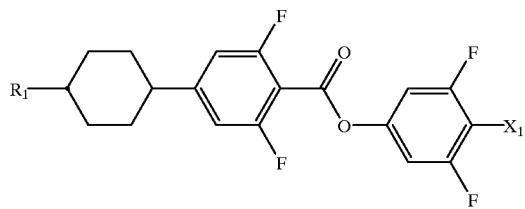
(3-61)
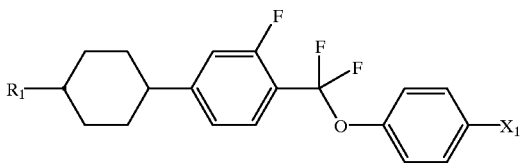
(3-62)
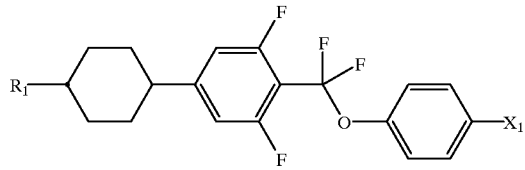
(3-63)
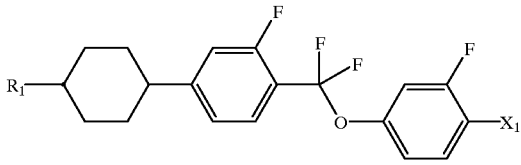
(3-64)
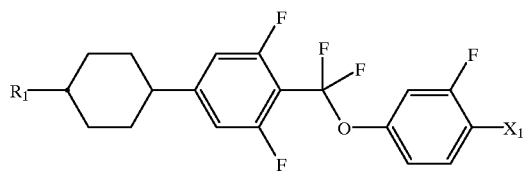
(3-65)
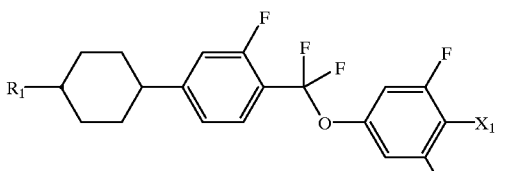
(3-66)
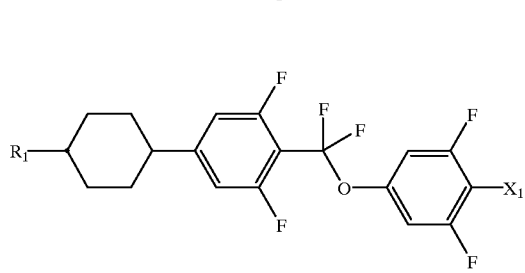
(3-67)
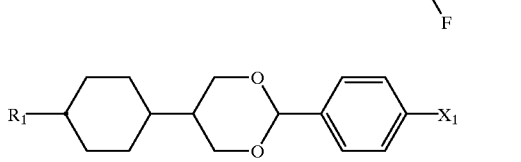
(3-68)
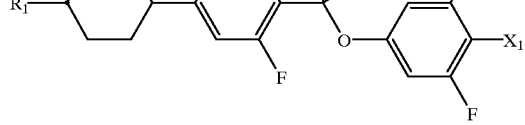
(3-69)
(4-1)
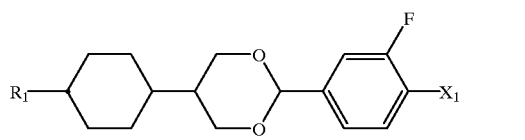
(4-2)
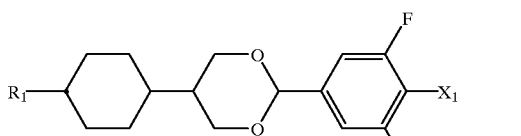
(4-3)
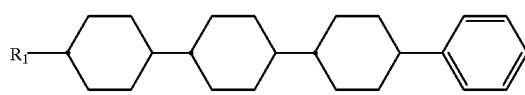
(4-4)
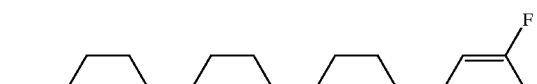
(4-5)
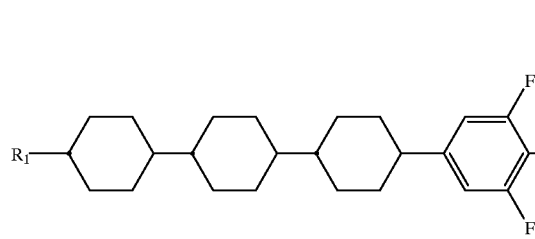
(4-6)
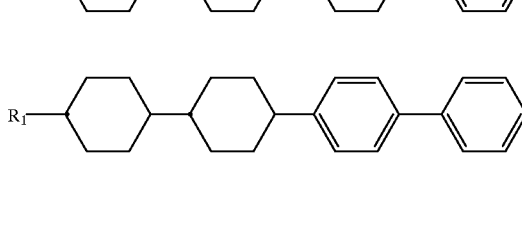

-continued
(4-7)
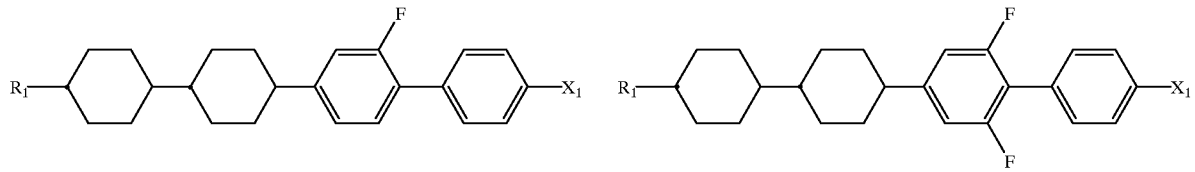
(4-8)
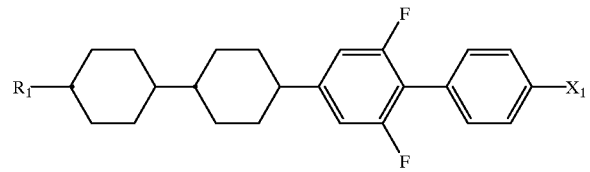
(4-9)
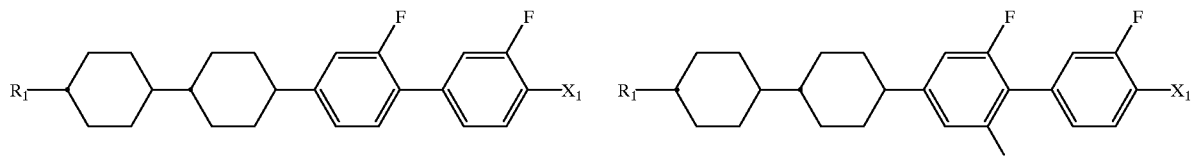
(4-10)
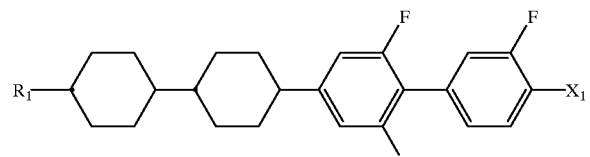
(4-11)
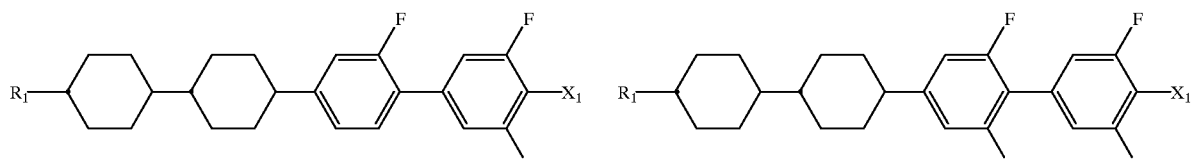
(4-12)
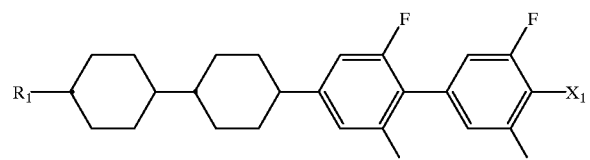
(4-13)
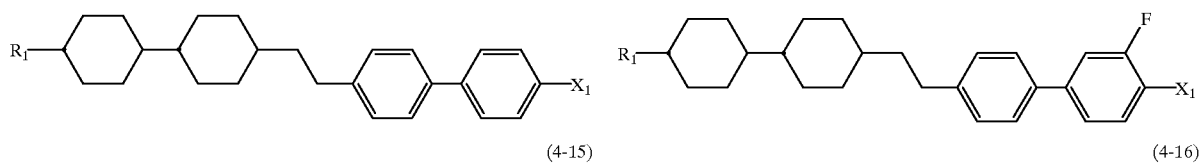
(4-14)
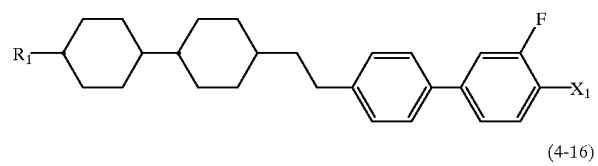
(4-15)
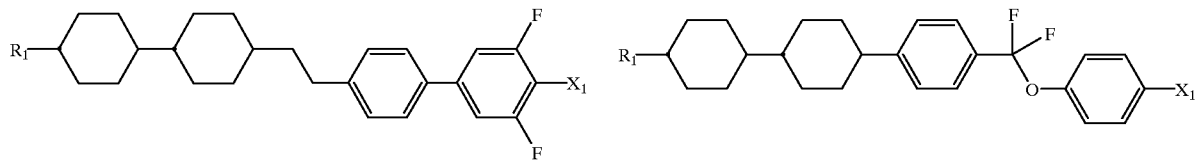
(4-16)
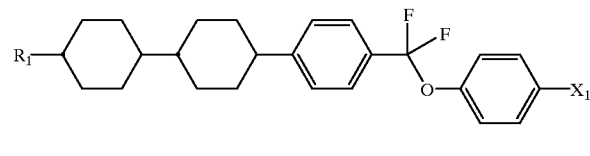
(4-17)
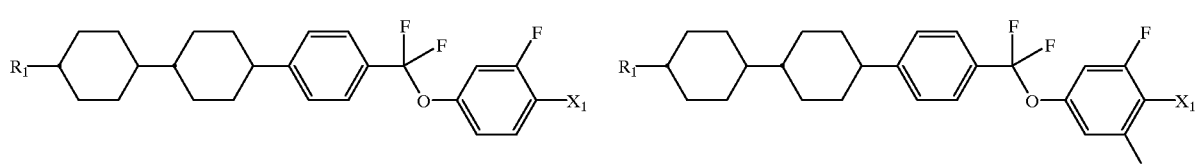
(4-18)
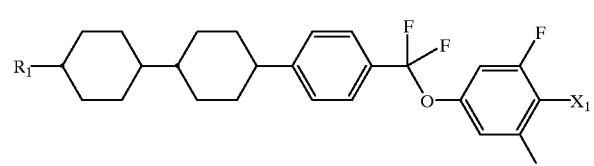
(4-19)
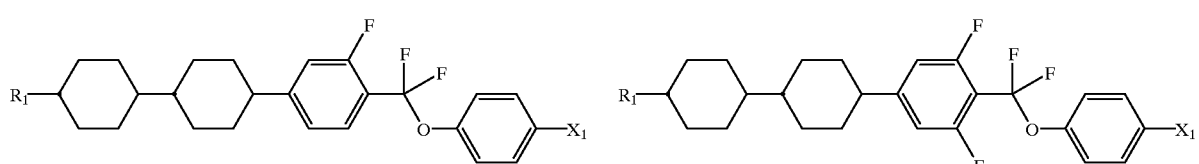
(4-20)
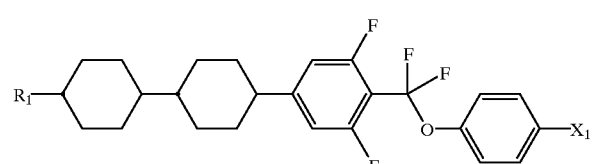
(4-21)
(4-22)
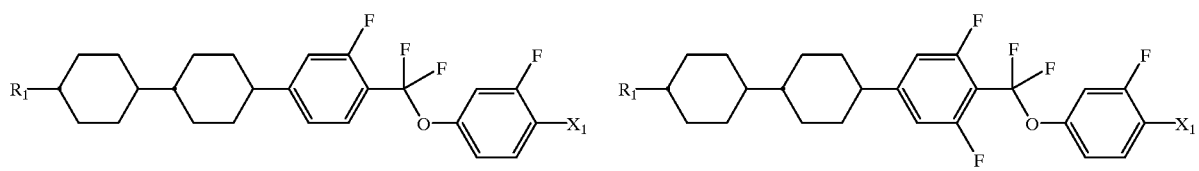

(4-23)
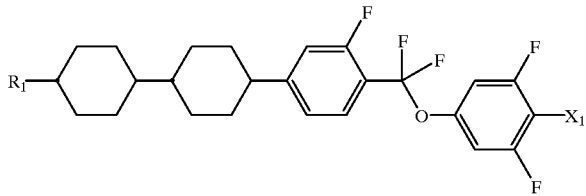

(4-24)
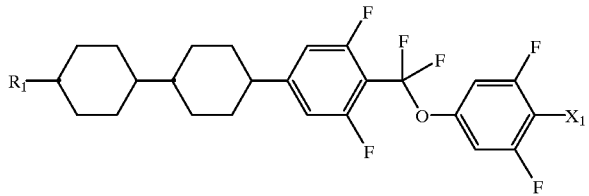

wherein $R_1$ and $X_1$ have the same meaning as described above.

The compounds represented by general formula (2)–(4) have positive dielectric anisotropy values, excellent thermal and chemical stability, and are especially useful for preparing liquid crystal compositions for TFT which require high reliability, i.e. high voltage holding ratio and high specific resistance.

For the preparation of liquid crystal compositions for TFT, the quantities of the compounds represented by general formula (2)–(4) may be within the range of 0.1 to 99.9% by weight, preferably 10 to 97% by weight, and more preferably 40 to 95% by weight relative to the total weight of the liquid crystal composition. The compounds represented by general formula (7)–(9) may further be combined for adjustment of viscosity.

The compounds represented by general formula (2)–(4) may also be used for the preparation of liquid crystal compositions for STN and TN. The quantities of the compounds are preferably 50% by weight or less.

As the compounds represented by general formula (5) or (6), the following compounds are preferably used.

(5-1)
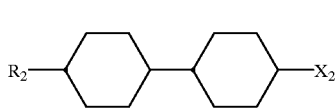

(5-2)
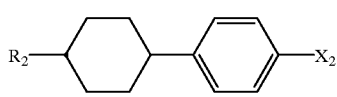

(5-3)
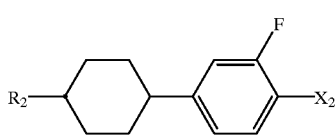

(5-4)
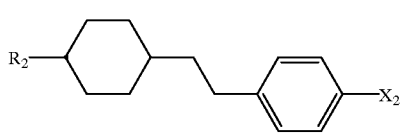

(5-5)
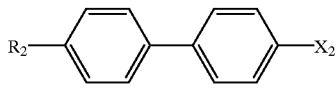

(5-6)
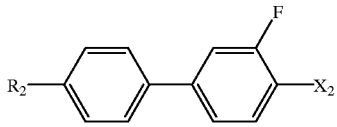

(5-7)
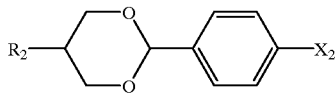

(5-8)
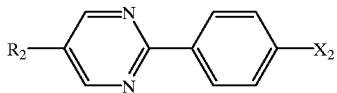

(5-9)
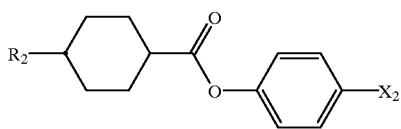

(5-10)
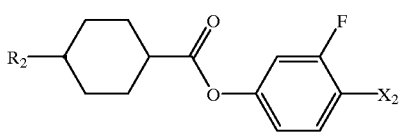

(5-11)
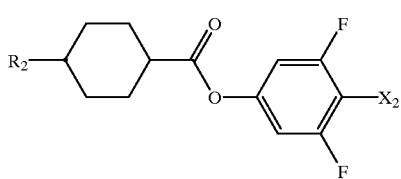

(5-12)
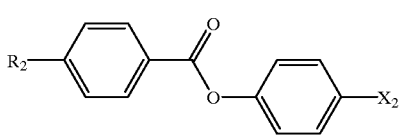

-continued
(5-13)
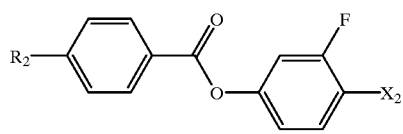
(5-14)
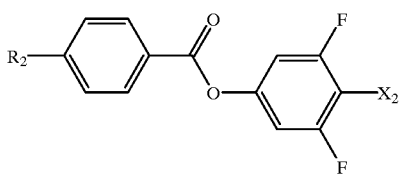
(5-15)
(5-16)
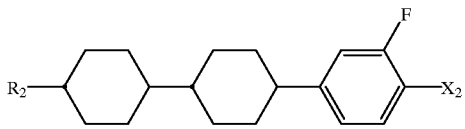
(5-17)
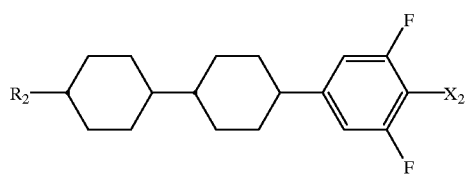
(5-18)
(5-19)
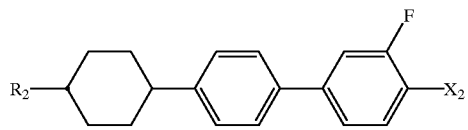
(5-20)
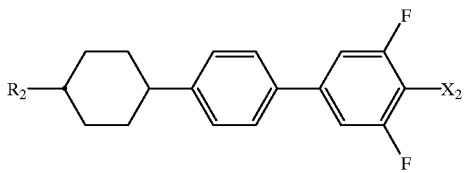
(5-21)
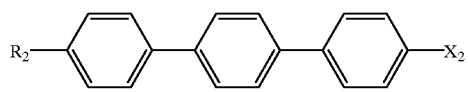
(5-22)
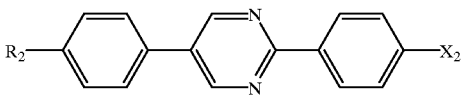
(5-23)
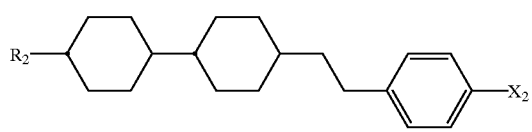
(5-24)
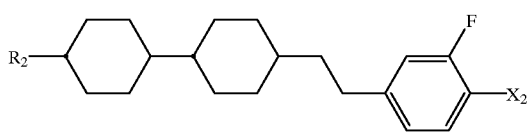
(5-25)
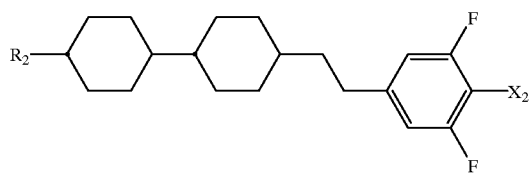
(5-26)
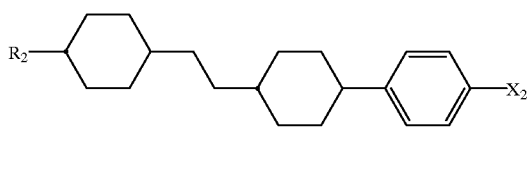
(5-27)
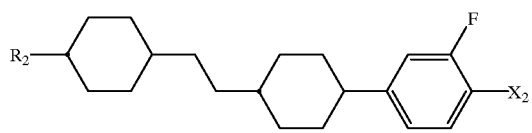
(5-28)
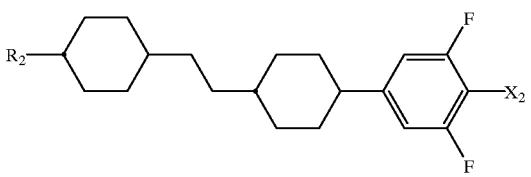
(5-29)
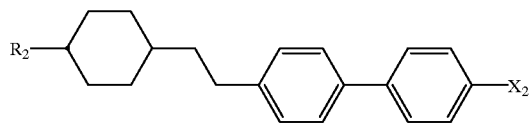
(5-30)
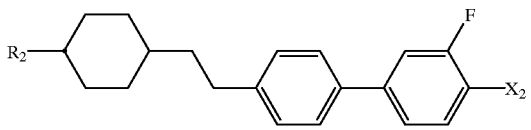

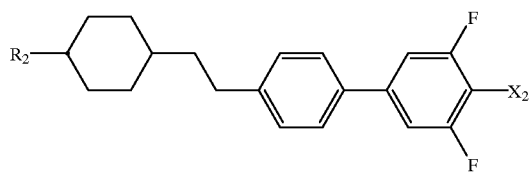
(5-31)

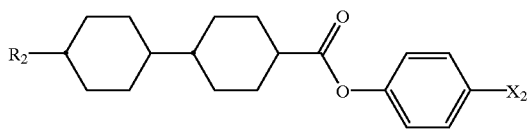
(5-32)

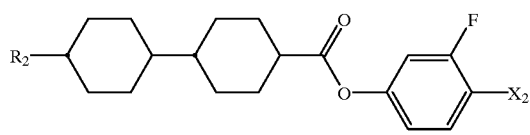
(5-33)

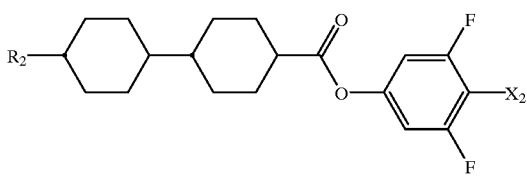
(5-34)

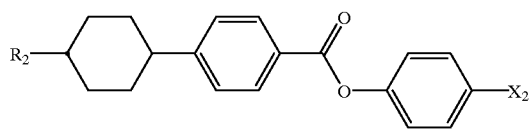
(5-35)

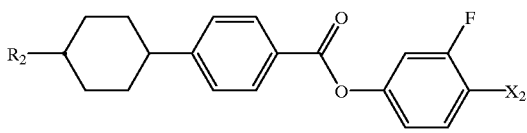
(5-36)

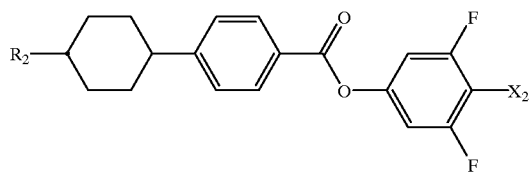
(5-37)

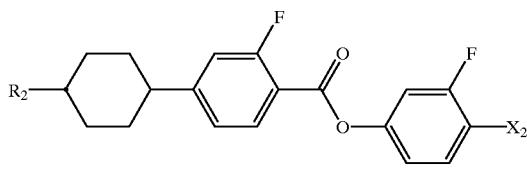
(5-38)

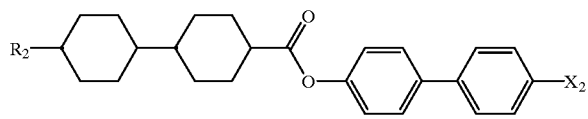
(5-39)

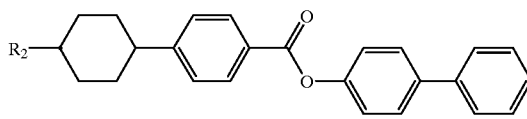
(5-40)

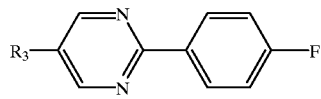
(6-1)

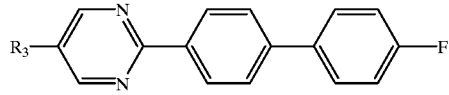
(6-2)

(6-3)

wherein $R_2$, $R_3$ and $X_2$ have the same meaning as shown in the above.

The compounds represented by general formula (5) or (6) have high positive dielectric anisotropy values, and are used especially for lowering the threshold voltage of the liquid crystal composition. The compounds are also used for adjusting optical anisotropy values and expanding the nematic range through, for example, raising clearing points. Further, the compounds are used to prepare liquid crystal compositions for STN and TN to improve the steepness of their voltage-transmittance correlation curve.

The compounds represented by general formula (5) or (6) are especially useful for preparing liquid crystal compositions for STN and TN.

When the quantity of the compounds represented by general formula (5) or (6) is increased, the threshold voltage of the liquid crystal compositions is lowered and the viscosity of increased. Accordingly, so long as the viscosity of the liquid crystal composition satisfies requirements, use of such compounds in large quantities is advantageous for low-voltage operation. The quantity of the compounds represented by general formula (5) or (6), in case of preparation of liquid crystal compositions for STN or TN, may be within the range of 0.1 to 99.9% by weight, preferably 10–97% by weight, and more preferably 40–95% by weight.

Preferred compounds represented by general formulae (7)–(9) may be exemplified below.

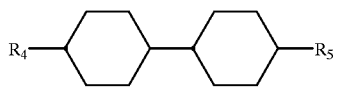 (7-1)
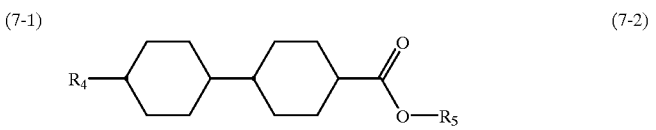 (7-2)
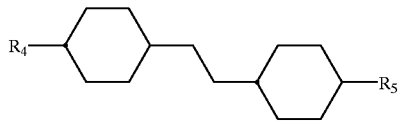 (7-3)
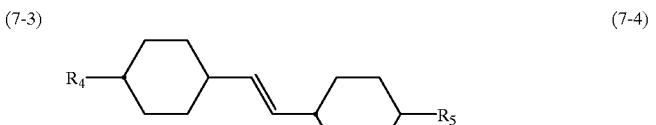 (7-4)
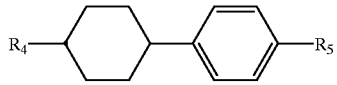 (7-5)
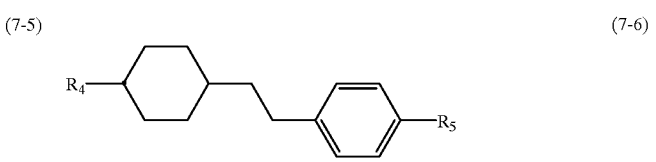 (7-6)
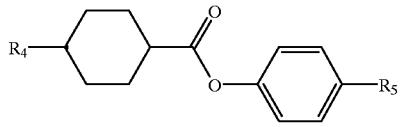 (7-7)
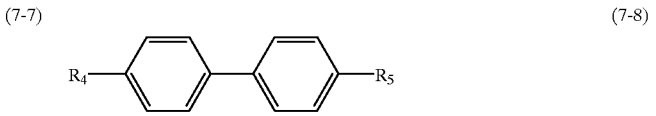 (7-8)
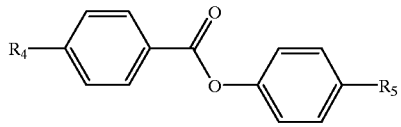 (7-9)
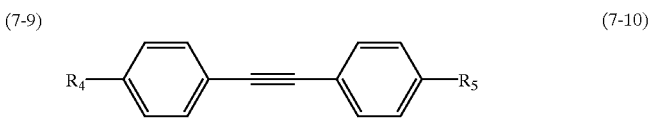 (7-10)
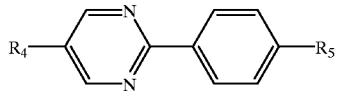 (7-11)
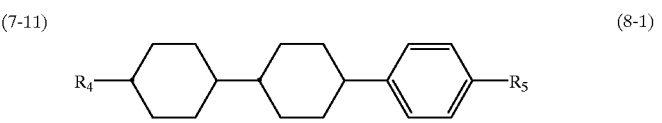 (8-1)
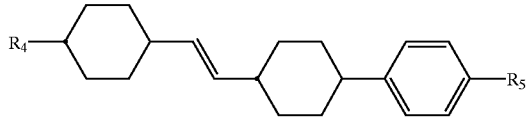 (8-2)
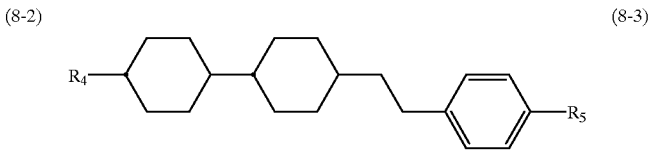 (8-3)
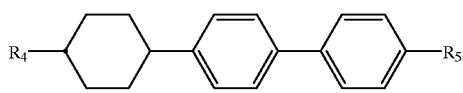 (8-4)
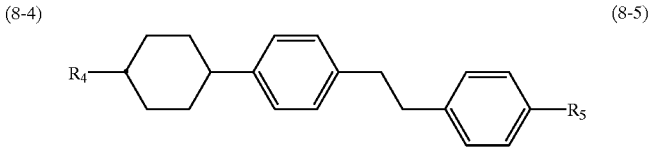 (8-5)
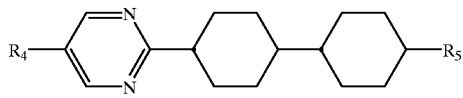 (8-6)
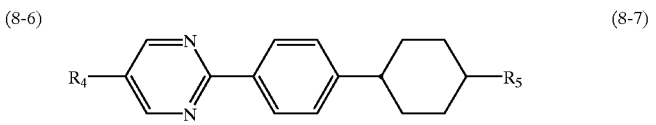 (8-7)
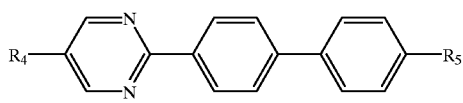 (8-8)
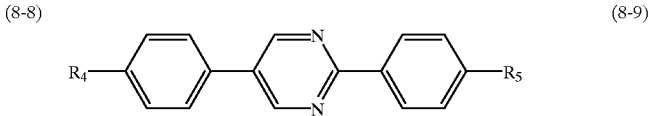 (8-9)
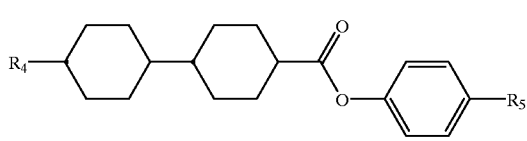 (8-10)
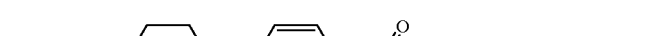
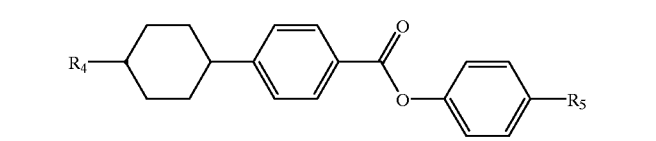 (8-11)

-continued (8-12) 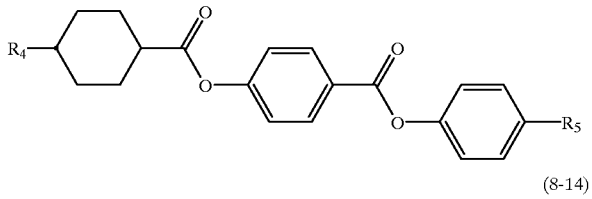

(8-13) 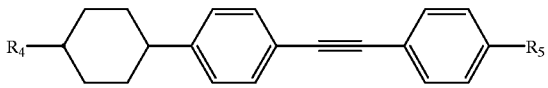

(8-14) 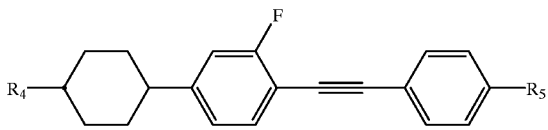

(8-15) 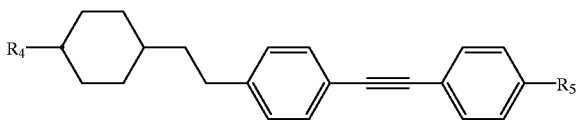

(8-16) 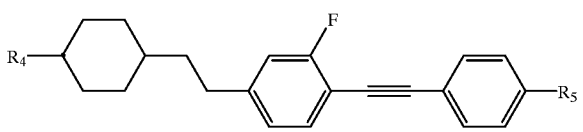

(8-17) 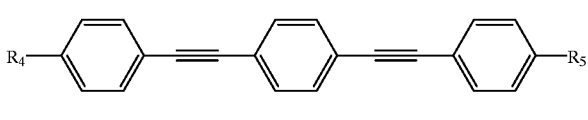

(8-18) 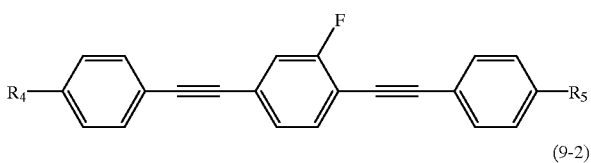

(9-1) 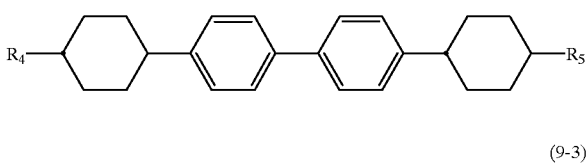

(9-2) 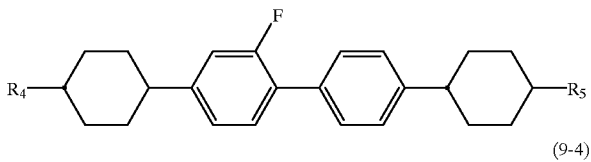

(9-3) 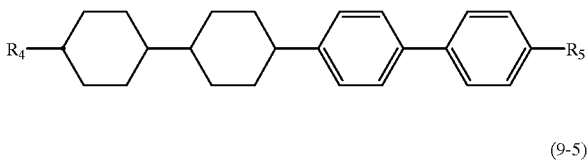

(9-4) 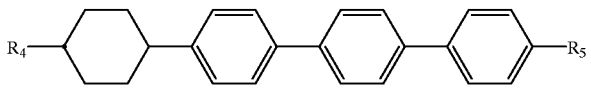

(9-5) 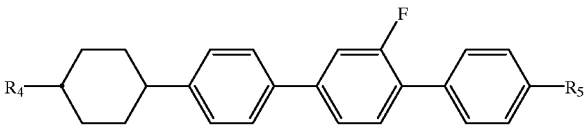

(9-6)

wherein $R_4$ and $R_5$ have the same meaning as described above.

The compounds represented by general formulae (7)–(9) have small absolute values of dielectric anisotropy, and these are nearly neutral. The compounds represented by general formula (7) are mainly used for adjusting viscosity and optical anisotropy values. The compounds represented by general formula (8) or (9) are mainly used for expanding the nematic range through, for example, raising clearing points or adjusting optical anisotropy values.

Increase in the quantity of the compounds represented by general formulae (7)–(9) increases the threshold voltage and lowers the viscosity of the liquid crystal composition. Therefore, so long as the threshold voltage of the liquid crystal composition satisfies requirements, use of the compounds in large quantities is preferred. The quantity of the compounds represented by general formulae (7)–(9), in case of preparation of liquid crystal compositions for TFT, may be preferably 40% by weight or less, more preferably 35% by weight or less. In case of preparation of liquid crystal compositions for STN and TN, it may be preferably 70% by weight or less, and more preferably 60% by weight or less.

Moreover, in the present invention, except in special cases such as liquid crystal compositions for an OCB (Optically Compensated Birefringence) mode, an optically active compound is normally added to the liquid crystal composition of the present invention for adjusting the required twist angle by inducing formation of the helical structure of the liquid crystal composition, and for preventing reverse twist. Although any known optically active compounds may be used in the present invention for the above purposes, as preferred compounds, the following optically active compounds may be exemplified.

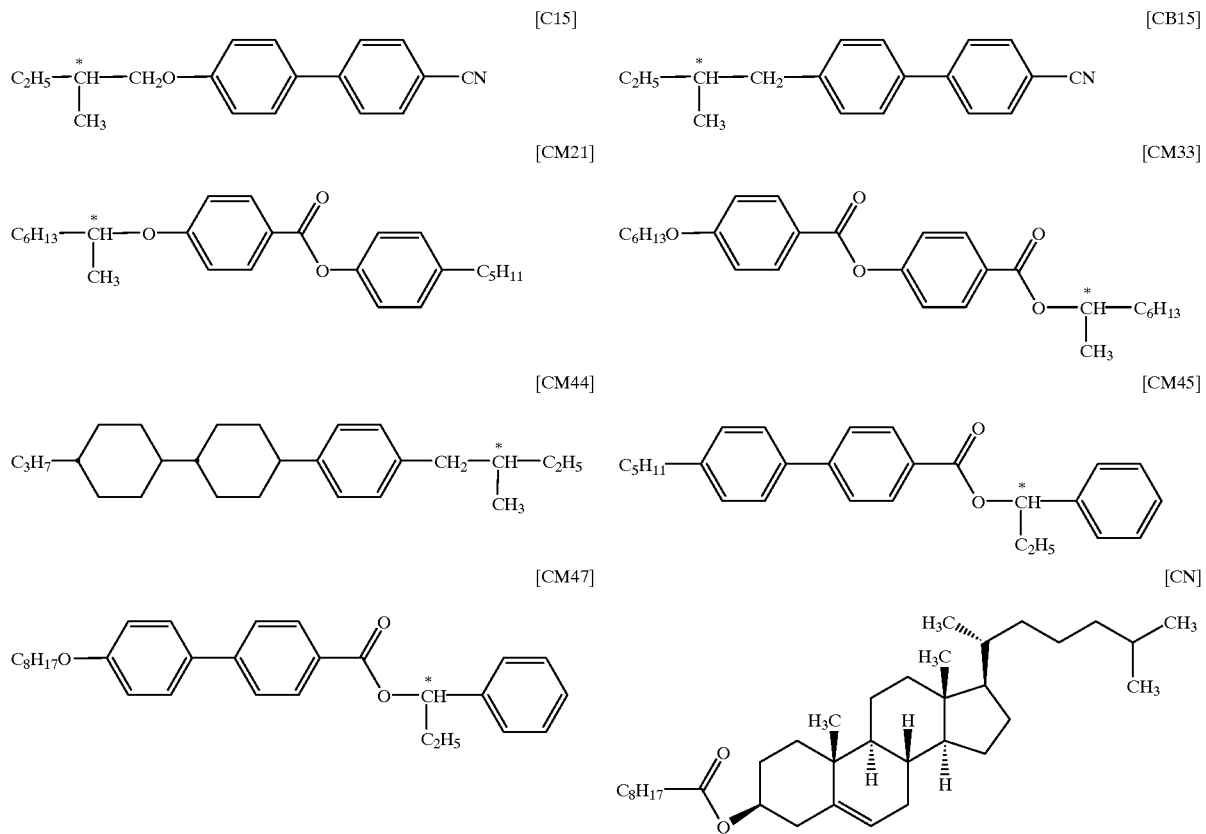

In the liquid crystal compositions of the present invention, the pitch of twist is adjusted by addition of these optically active compounds. The pitch of twist if preferably adjusted within the range of 40–200 μm for liquid crystal compositions for TFT and TN, and 6–20 μm for liquid crystal compositions for STN. In case of a bistable TN mode, it is preferably adjusted within the range of 1.5–4 μm. For adjustment of the temperature dependence of the pitch, two or more optically active compounds may be added.

The liquid crystal compositions of the present invention are prepared by well known methods. In general, a method in which various compounds are dissolved in each other at high temperature is used.

Furthermore, the liquid crystal compositions of the present invention may be used as those for the guest-host (GH) mode by adding dichroic dyes such as melocyanin, styryl, azo, azomethyne, azoxy, quinophthalon, anthraquinone and tetrazine types. Moreover, the compositions may be used for NCAP, which is prepared by microcapsulation of a nematic liquid crystal, or for a polymer dispersion liquid crystal device (PDLCD) represented by a polymer network liquid crystal device (PNLCD), which a polymer of tridimensional network structure is prepared in liquid crystal. In addition, the liquid crystal compositions may be used for an electrically controlled birefringence (ECB) mode or a dynamic scattering (DS) mode.

The following liquid crystal compositions containing the compounds of the present invention can be exemplified. Moreover, the compounds in the composition examples and undermentioned working examples are represented by brief symbols in accordance with the rules expressed in the following tables, and the numbers of the compounds are the same as those in the following examples. Further, in the composition examples and working examples, except where noted otherwise, "%" means "% by weight."

Rc—Aa—Za———Zn—Ao—Rd

| Left end group Rc | |
|---|---|
| $C_aH_{2a+1}-$ | a- |
| $C_aH_{2a+1}O-$ | aO- |
| $C_aH_{2a+1}OC_bH_{2b}-$ | aOb- |
| $C_aH_{2a+1}OC_bH_{2b}O-$ | aObO- |
| $C_{a+1}H_{2(a-1)+1}C(C_bH_{2b+1})HC_cH_{2c}-$ | a(b)c- |
| $CFH_2C_{a-1}H_{2(a-1)}-$ | Fa- |
| $CF_2HC_{a-1}H_{2(a-1)}-$ | FFa- |
| $CF_3C_{a-1}H_{2(a-1)}-$ | FFFa- |
| $CFH_2C_{a-1}H_{2(a-1)}O-$ | FaO- |
| $CFH_2C_{a-1}H_{2(a-1)}OC_bH_{2b}-$ | FaOb- |
| $C_aH_{2a+1}CFHC_bH_{2b}-$ | a(F)b- |
| $C_aH_{2a+1}CF_2C_bH_{2b}-$ | a(FF)b- |
| $C_aH_{2a+1}CH=CHC_bH_{2b}-$ | aVb- |
| $C_aH_{2a+1}CH=CHC_bH_{2b}CH=CHC_cH_{2c}-$ | aVbVc- |
| $C_aH_{2a+1}CH=CHC_bH_{2b}OC_cH_{2c}-$ | aVbOc- |
| $C_aH_{2a+1}OC_bH_{2b}CH=CHC_cH_{2c}-$ | aObVc- |
| $CFH_2C_{a-1}H_{2(a-1)}CH=CHC_bH_{2b}-$ | FaVb- |
| $FFC=CHC_aH_{2a}-$ | FFVa- |
| $F(CN)C=CHC_aH_{2a}-$ | FCVa- |
| Bonding group Za~Zn | |
| $-(CH_2)_a-$ | a |
| $-CH_2O-$ | $CH_2O$ |
| $-OCH_2-$ | $OCH_2$ |
| $-C_3H_6O-$ | $C_3H_6O$ |
| $-OC_3H_6-$ | $OC_3H_6$ |
| $-COO-$ | E |
| $-C{\equiv}C-$ | T |

-continued

| Rc—Aa—Za— ---- —Zn—Ao—Rd | |
|---|---|
| —CH=CH— | V |
| —CF₂O— | CF2O |
| —OCF₂— | OCF2 |

Ring structure Aa~Ao

| | | | |
|---|---|---|---|
|  | B | 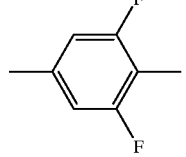 | B(F,F) |
| 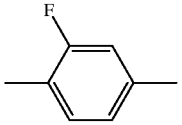 | B(2F) | 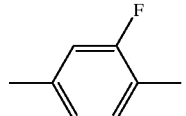 | B(F,Cl) |
| 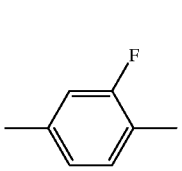 | B(F) | 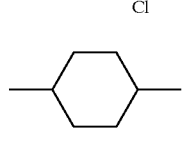 | H |
| 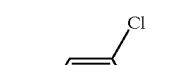 | B(Cl) | 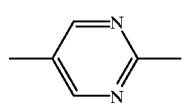 | Py |
| 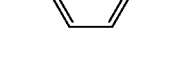 | B(2,3F) |  | D |
| 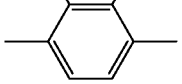 | B(2,3Cl) | 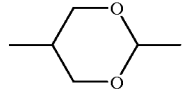 | Ch |

Right end group Rd

| | |
|---|---|
| —F | —F |
| —Cl | —CL |
| —CN | —C |
| —CF₃ | —CF3 |
| —OCF₃ | —OCF3 |
| —OCF₂H | —OCF2H |
| —OCF₂CF₂H | —OCF2CF2H |
| —OCF₂CFHCF₃ | —OCF2CFHCF3 |
| —C$_w$H$_{2w+1}$ | -w |
| —OC$_w$H$_{2w+1}$ | -Ow |
| —C$_w$H$_{2w}$CH=CH₂ | -wV |
| —C$_w$H$_{2w}$CH=CHC$_x$H$_{2x+1}$ | -wVx |
| —COOCH₃ | -EMe |
| —C$_w$H$_{2w}$CH=CHC$_x$H$_{2x}$F | -wVxF |
| —CH=CF₂ | -VFF |
| —C$_w$H$_{2w}$CH=CF₂ | -wVFF |
| —C≡C—CN | -TC |

Composition Example 1

| | | |
|---|---|---|
| 3-BB(F,F)B(F,F)—F | (Compound No.26) | 5.0% |
| 3-B(F)B(F)B(F,F)—F | (Compound No.14) | 5.0% |
| 3-B(F)B(F,F)B(F)—F | (Compound No.54) | 5.0% |
| 1V2-BEB(F,F)—C | | 5.0% |
| 3-HB—C | | 25.0% |
| 1-BTB-3 | | 5.0% |
| 3-HH-4 | | 11.0% |
| 3-HHB-1 | | 6.0% |
| 3-HHB-3 | | 9.0% |
| 3-H2BTB-2 | | 4.0% |
| 3-H2BTB-3 | | 4.0% |
| 3-H2BTB-4 | | 4.0% |
| 3-HB(F)TB-2 | | 6.0% |
| 3-HB(F)TB-3 | | 6.0% |

Composition Example 2

| | | |
|---|---|---|
| 3-BB(F,F)B(F)—OCF₃ | (Compound No.1) | 6.0% |
| 3-B(F)B(F,F)B(F)—CL | (Compound No.57) | 6.0% |
| V2-HB—C | | 12.0% |
| 1V2-HB—C | | 12.0% |
| 3-HB—C | | 12.0% |
| 3-HB(F)—C | | 5.0% |
| 2-BTB-1 | | 2.0% |
| 3-HH-4 | | 8.0% |
| 3-HH—VFF | | 6.0% |
| 2-HHB—C | | 3.0% |
| 3-HHB—C | | 6.0% |
| 3-HB(F)TB-2 | | 8.0% |
| 3-H2BTB-2 | | 5.0% |
| 3-H2BTB-3 | | 5.0% |
| 3-H2BTB-4 | | 4.0% |

Composition Example 3

| | | |
|---|---|---|
| 3-BB(F,F)B(F)—OCF₃ | (Compound No.1) | 5.0% |
| 3O1-BEB(F)—C | | 15.0% |
| 4O1-BEB(F)—C | | 13.0% |
| 5O1-BEB(F)—C | | 13.0% |
| 2-HHB(F)—C | | 15.0% |
| 3-HHB(F)—C | | 15.0% |
| 3-HB(F)TB-2 | | 4.0% |
| 3-HB(F)TB-3 | | 4.0% |
| 3-HB(F)TB-4 | | 4.0% |
| 3-HHB-1 | | 8.0% |
| 3-HHB—O1 | | 4.0% |

Composition Example 4

| | | |
|---|---|---|
| 3-B(F)B(F)B(F,F)—F | (Compound No.14) | 4.0% |
| 3-B(F)B(F,F)B(F)—CL | (Compound No.57) | 4.0% |
| 5-PyB—F | | 4.0% |
| 3-PyB(F)—F | | 4.0% |
| 2-BB—C | | 5.0% |
| 4-BB—C | | 4.0% |
| 5-BB—C | | 5.0% |
| 2-PyB-2 | | 2.0% |
| 3-PyB-2 | | 2.0% |
| 4-PyB-2 | | 2.0% |
| 6-PyB—O5 | | 3.0% |
| 6-PyB—O6 | | 3.0% |
| 6-PyB—O7 | | 3.0% |
| 6-PyB—O8 | | 3.0% |
| 3-PyBB—F | | 6.0% |
| 4-PyBB—F | | 6.0% |
| 5-PyBB—F | | 6.0% |
| 3-HHB-1 | | 6.0% |
| 3-HHB-3 | | 8.0% |
| 2-H2BTB-4 | | 5.0% |
| 3-H2BTB-2 | | 5.0% |
| 3-H2BTB-3 | | 5.0% |
| 3-H2BTB-4 | | 5.0% |

Composition Example 5

| | | |
|---|---|---|
| 3-B(F)B(F)B(F,F)—F | (Compound No.14) | 10.0% |
| 3-BB(F,F)B(F)—OCF₃ | (Compound No.1) | 4.0% |
| 3-DB—C | | 10.0% |
| 2-BEB—C | | 12.0% |
| 3-PyB(F)—F | | 6.0% |
| 3-HEB—O4 | | 8.0% |

| | | |
|---|---|---|
| 4-HEB—O2 | | 6.0% |
| 5-HEB—O1 | | 6.0% |
| 3-HEB—O2 | | 5.0% |
| 5-HEB—O2 | | 4.0% |
| 5-HEB-5 | | 5.0% |
| 4-HEB-5 | | 5.0% |
| 1O—BEB-2 | | 4.0% |
| 3-HHB-1 | | 6.0% |
| 3-HHEBB—C | | 3.0% |
| 3-HBEBB—C | | 3.0% |
| 5-HBEBB—C | | 3.0% |
| Composition Example 6 | | |
| 3-B(F)B(F,F)B(F)—CFH₂ | (Compound No.71) | 3.0% |
| 3-BB(F,F)B(F,F)—F | (Compound No.26) | 4.0% |
| 3-B(F)B(F,F)B(F)—F | (Compound No.54) | 4.0% |
| 3-HB—C | | 18.0% |
| 1O1-HB—C | | 10.0% |
| 3-HB(F)—C | | 10.0% |
| 2-PyB-2 | | 2.0% |
| 3-PyB-2 | | 2.0% |
| 4-PyB-2 | | 2.0% |
| 1O1-HH-3 | | 3.0% |
| 2-BTB—O1 | | 3.0% |
| 3-HHB-1 | | 7.0% |
| 3-HHB—F | | 4.0% |
| 3-HHB—O1 | | 4.0% |
| 3-HB—O2 | | 8.0% |
| 3-H2BTB-2 | | 3.0% |
| 3-H2BTB-3 | | 3.0% |
| 2-PyBH-3 | | 4.0% |
| 3-PyBH-3 | | 3.0% |
| 3-PyBB-2 | | 3.0% |
| Composition Example 7 | | |
| 3-B(F)B(F)B(F,F)—OCF₂H | (Compound No.18) | 5.0% |
| 3-B(F)B(F)B(F,F)—CF₂H | (Compound No.22) | 4.0% |
| 3O1-BEB(F)—C | | 12.0% |
| 1V2-BEB(F,F)—C | | 10.0% |
| 3-HH-EMe | | 10.0% |
| 3-HB—O2 | | 18.0% |
| 7-HEB—F | | 2.0% |
| 3-HHEB—F | | 2.0% |
| 5-HHEB—F | | 2.0% |
| 3-HBEB—F | | 4.0% |
| 2O1-HBEB(F)—C | | 2.0% |
| 3-HB(F)EB(F)—C | | 2.0% |
| 3-HBEB(F,F)—C | | 2.0% |
| 3-HHB—F | | 4.0% |
| 3-HHB—O1 | | 4.0% |
| 3-HHB-3 | | 13.0% |
| 3-HEBEB—F | | 2.0% |
| 3-HEBEB-1 | | 2.0% |
| Composition Example 8 | | |
| 3-B(F)B(F)B(F,F)—F | (Compound No.14) | 5.0% |
| 5-BEB(F)—C | | 5.0% |
| V—HB—C | | 11.0% |
| 5-PyB—C | | 6.0% |
| 4-BB-3 | | 6.0% |
| 3-HH-2V | | 10.0% |
| 5-HH—V | | 11.0% |
| V—HHB-1 | | 7.0% |
| V2-HHB-1 | | 15.0% |
| 3-HHB-1 | | 9.0% |
| 1V2-HBB-2 | | 10.0% |
| 3-HHEBH-3 | | 5.0% |
| Composition Example 9 | | |
| 3-BB(F,F)B(F,F)—F | (Compound No.26) | 4.0% |
| 2O1-BEB(F)—C | | 5.0% |
| 3O1-BEB(F)—C | | 12.0% |
| 5O1-BEB(F)—C | | 4.0% |
| 1V2-BEB(F,F)—C | | 16.0% |
| 3HB—O2 | | 10.0% |
| 3-HH-4 | | 3.0% |
| 3-HHB-F | | 3.0% |
| 3-HHB-1 | | 8.0% |
| 3-HHB—O1 | | 4.0% |
| 3-HBEB—F | | 4.0% |
| 3-HHEB—F | | 7.0% |
| 5-HHEB—F | | 7.0% |
| 3-H2BTB-2 | | 4.0% |
| 3-H2BTB-3 | | 4.0% |
| 3-HB(F)TB-2 | | 5.0% |
| Composition Example 10 | | |
| 3-B(F)B(F,F)B(F)—F | (Compound No.54) | 8.0% |
| 2-BEB—C | | 12.0% |
| 3-BEB—C | | 4.0% |
| 4-BEB—C | | 6.0% |
| 3-HB—C | | 20.0% |
| 3-HEB—O4 | | 12.0% |
| 4-HEB—O2 | | 8.0% |
| 5-HEB—O1 | | 8.0% |
| 3-HEB—O2 | | 6.0% |
| 5-HEB—O2 | | 5.0% |
| 3-HHB-1 | | 7.0% |
| 3-HHB—O1 | | 4.0% |
| Composition Example 11 | | |
| 3-B(F)B(F,F)B(F)—CL | (Compound No.57) | 5.0% |
| 2-BEB—C | | 10.0% |
| 5-BB—C | | 12.0% |
| 7-BB—C | | 7.0% |
| 1-BTB-3 | | 7.0% |
| 2-BTB-1 | | 5.0% |
| 1O—BEB-2 | | 10.0% |
| 1O—BEB-5 | | 12.0% |
| 2-HHB-1 | | 5.0% |
| 3-HHB—F | | 4.0% |
| 3-HHB-1 | | 7.0% |
| 3-HHB—O1 | | 4.0% |
| 3-HHB-3 | | 13.0% |
| Composition Example 12 | | |
| 3-BB(F,F)B(F)—OCF₃ | (Compound No.1) | 7.0% |
| 2-HHB(F)—F | | 17.0% |
| 3-HHB(F)—F | | 17.0% |
| 5-HHB(F)—F | | 16.0% |
| 2-H2HB(F)—F | | 10.0% |
| 3-H2HB(F)—F | | 5.0% |
| 5-H2HB(F)—F | | 10.0% |
| 2-HBB(F)—F | | 6.0% |
| 3-HBB(F)—F | | 6.0% |
| 5-HBB(F)—F | | 6.0% |
| Composition Example 13 | | |
| 3-BB(F,F)B(F)—OCF₃ | (Compound No.1) | 3.0% |
| 3-B(F)B(F,F)B(F)—CL | (Compound No.57) | 3.0% |
| 7-HB(F)—F | | 5.0% |
| 5-H2B(F)—F | | 5.0% |
| 3-HB—O2 | | 10.0% |
| 3-HH-4 | | 5.0% |
| 2-HHB(F)—F | | 10.0% |
| 3-HHB(F)—F | | 10.0% |
| 5-HHB(F)—F | | 10.0% |
| 3-H2HB(F)—F | | 5.0% |
| 2-HBB(F)—F | | 3.0% |
| 3-HBB(F)—F | | 3.0% |
| 2-H2BB(F)—F | | 5.0% |
| 3-H2BB(F)—F | | 6.0% |
| 3-HHB-1 | | 8.0% |
| 3-HHB—O1 | | 5.0% |
| 3-HHB-3 | | 4.0% |
| Composition Example 14 | | |
| 3-BB(F,F)B(F,F)—F | (Compound No.26) | 8.0% |
| 3-B(F)B(F)B(F,F)—F | (Compound No.14) | 8.0% |
| 3-B(F)B(F)B(F,F)—OCF₂H | (Compound No.18) | 5.0% |
| 3-B(F)B(F)B(F,F)—CF₂H | (Compound No.22) | 5.0% |
| 7-HB(F,F)—F | | 3.0% |
| 3-HB—O2 | | 7.0% |
| 2-HHB(F)—F | | 10.0% |
| 3-HHB(F)—F | | 10.0% |
| 5-HHB(F)—F | | 10.0% |
| 2-HBB(F)—F | | 9.0% |
| 3-HBB(F)—F | | 9.0% |

-continued

| | | |
|---|---|---|
| 2-HBB—F | | 4.0% |
| 3-HBB—F | | 4.0% |
| 5-HBB—F | | 3.0% |
| 3-HBB(F,F)—F | | 5.0% |
| Composition Example 15 | | |
| 3-BB(F,F)B(F,F)—F | (Compound No.26) | 4.0% |
| 3-B(F)B(F)B(F,F)—F | (Compound No.14) | 4.0% |
| 3-B(F)B(F,F)B(F)—F | (Compound No.54) | 4.0% |
| 7-HB(F,F)—F | | 4.0% |
| 3-H2HB(F,F)—F | | 12.0% |
| 4-H2HB(F,F)—F | | 10.0% |
| 5-H2HB(F,F)—F | | 10.0% |
| 3-HHB(F,F)—F | | 10.0% |
| 4-HHB(F,F)—F | | 5.0% |
| 3-HH2B(F,F)—F | | 15.0% |
| 5-HH2B(F,F)—F | | 10.0% |
| 3-HBB(F,F)—F | | 12.0% |
| Composition Example 16 | | |
| 3-B(F)B(F)B(F,F)—F | (Compound No.14) | 5.0% |
| 3-BB(F,F)B(F)—OCF₃ | (Compound No.1) | 5.0% |
| 3-BB(F,F)B(F,F)—F | (Compound No.26) | 5.0% |
| 3-B(F)B(F,F)B(F)—F | (Compound No.54) | 3.0% |
| 7-HB(F,F)—F | | 5.0% |
| 3-H2HB(F,F)—F | | 12.0% |
| 3-HHB(F,F)—F | | 10.0% |
| 3-HBB(F,F)—F | | 10.0% |
| 3-HHEB(F,F)—F | | 10.0% |
| 4-HHEB(F,F)—F | | 3.0% |
| 5-HHEB(F,F)—F | | 3.0% |
| 3-HBEB(F,F)—F | | 5.0% |
| 5-HBEB(F,F)—F | | 3.0% |
| 3-HDB(F,F)—F | | 15.0% |
| 3-HHBB(F,F)—F | | 6.0% |
| Composition Example 17 | | |
| 3-BB(F,F)B(F)—OCF₃ | (Compound No.1) | 7.0% |
| 3-B(F)B(F)B(F,F)—F | (Compound No.14) | 7.0% |
| 3-HB—CL | | 10.0% |
| 5-HB—CL | | 4.0% |
| 7-HB—CL | | 4.0% |
| 1O1-HH-5 | | 5.0% |
| 2-HBB(F)—F | | 8.0% |
| 3-HBB(F)—F | | 8.0% |
| 4-HHB—CL | | 8.0% |
| 5-HHB—CL | | 8.0% |
| 3-H2HB(F)—CL | | 4.0% |
| 3-HBB(F,F)—F | | 10.0% |
| 5-H2BB(F,F)—F | | 9.0% |
| 3-HB(F)VB-2 | | 4.0% |
| 3-HB(F)VB-3 | | 4.0% |
| Composition Example 18 | | |
| 3-B(F)B(F)B(F,F)—F | (Compound No.14) | 4.0% |
| 3-B(F)B(F)B(F,F)—OCF₂H | (Compound No.18) | 4.0% |
| 3-BB(F)B(F)—OCF₃ | (Compound No.1) | 5.0% |
| 3-B(F)B(F)B(F,F)B(F)—CL | (Compound No.57) | 5.0% |
| 3-HHB(F,F)—F | | 9.0% |
| 3-H2HB(F,F)—F | | 8.0% |
| 4-H2HB(F,F)—F | | 8.0% |
| 3-HBB(F,F)—F | | 21.0% |
| 5-HBB(F,F)—F | | 10.0% |
| 3-H2BB(F,F)—F | | 10.0% |
| 5-HHBB(F,F)—F | | 3.0% |
| 3-HH2BB(F,F)—F | | 3.0% |
| 5-HHEBB—F | | 2.0% |
| 1O1-HBBH-4 | | 4.0% |
| 1O1-HBBH-5 | | 4.0% |
| Composition Example 19 | | |
| 3-B(F)B(F,F)B(F)—CL | (Compound No.57) | 2.0% |
| 3-BB(F,F)B(F,F)—F | (Compound No.26) | 2.0% |
| 3-B(F)B(F)B(F,F)—F | (Compound No.14) | 2.0% |
| 3-BB(F,F)B(F)—OCF₃ | (Compound No.1) | 2.0% |
| 3-B(F)B(F)B(F,F)—OCF₂H | (Compound No.18) | 2.0% |
| 5-HB—F | | 12.0% |
| 6-HB—F | | 9.0% |
| 7-HB—F | | 7.0% |

-continued

| | | |
|---|---|---|
| 2-HHB—OCF₃ | | 7.0% |
| 3-HHB—OCF₃ | | 11.0% |
| 4-HHB—OCF₃ | | 7.0% |
| 5-HHB—OCF₃ | | 5.0% |
| 3-HH2B—OCF₃ | | 4.0% |
| 5-HH2B—OCF₃ | | 4.0% |
| 3-HHB(F,F)—OCF₃ | | 5.0% |
| 3-HBB(F)—F | | 10.0% |
| 3-HH2B(F)—F | | 3.0% |
| 3-HB(F)BH-3 | | 3.0% |
| 5-HBBH-3 | | 3.0% |
| Composition Example 20 | | |
| 3-B(F)B(F,F)B(F)—F | (Compound No.54) | 5.0% |
| 3-BB(F,F)B(F)—OCF₃ | (Compound No.1) | 2.0% |
| 3-B(F)B(F,F)B(F)—CFH₂ | (Compound No.71) | 2.0% |
| 5-H4HB(F,F)—F | | 7.0% |
| 5-H4HB—OCF₃ | | 13.0% |
| 3-H4HB(F,F)—CF₃ | | 8.0% |
| 5-H4HB(F,F)—CF₃ | | 8.0% |
| 3-HB—CL | | 6.0% |
| 5-HB—CL | | 4.0% |
| 2-H2BB(F)—F | | 5.0% |
| 3-H2BB(F)—F | | 10.0% |
| 5-HVHB(F,F)—F | | 5.0% |
| 3-HHB—OCF₃ | | 5.0% |
| 3-H2HB—OCF₃ | | 5.0% |
| V-HHB(F)—F | | 5.0% |
| 5-HHEB—OCF₃ | | 2.0% |
| 3-HBEB(F,F)—F | | 5.0% |
| 5-HH—V2F | | 3.0% |
| Composition Example 21 | | |
| 3-B(F)B(F,F)B(F)—CL | (Compound No.57) | 3.0% |
| 3-BB(F,F)B(F,F)—F | (Compound No.26) | 3.0% |
| 3-B(F)B(F)B(F,F)—F | (Compound No.14) | 3.0% |
| 2-HHB(F)—F | | 2.0% |
| 3-HHB(F)—F | | 2.0% |
| 5-HHB(F)—F | | 2.0% |
| 2-HBB(F)—F | | 6.0% |
| 3-HBB(F)—F | | 6.0% |
| 5-HBB(F)—F | | 10.0% |
| 2-H2BB(F)—F | | 9.0% |
| 3-H2BB(F)—F | | 9.0% |
| 3-HBB(F,F)—F | | 25.0% |
| 5-HBB(F,F)—F | | 10.0% |
| 1O1-HBBH-4 | | 5.0% |
| 1O1-HBBH-5 | | 5.0% |

BEST MODE FOR CARRYING OUT THE INVENTION

The following examples illustrate the present invention more specifically. In each example, C is a crystal, $S_A$ is a smectic A phase, $S_B$ is a smectic B phase, $S_X$ is a smectic phase wherein the phase constitution remains to be analyzed, N is a nematic phase, Iso is an isotropic phase, and the unit of phase transition temperature is ° C.

EXAMPLE 1

Preparation of 4'-propyl-2',6'-difluoro-3-fluoro-4-trifluoromethoxyterphenyl (in general formula (1), R is $C_3H_7$; $Y_1$, $Y_2$ and $Y_6$ are each H; $Y_3$, $Y_4$ and $Y_5$ are each F; and X is —OCF₃) (compounds No. 1)

(Step 1) Preparation of 4'-propyl-3,5-difluoro-4-iodobiphenyl

To a solution of 4'-propyl-3,5-diflurorbipheny 40.0 g (0.17 mol) in tetrahydrofuran (THF) 250 ml, n-BuLi 160 ml (0.25 mol) was added dropwise at a speed to keep −60° C. or less, and stirred for one hour at the same temperature. Then a solution of iodine 78.7 g (0.31 mol) in THF 300 ml was added dropwise at a speed to keep −60° C. or less, and the mixture was stirred for one hour at the same temperature. Then, a solution of iodine 78.7 g (0.31 mol) in THF 300 ml was added dropwise at a speed to keep −60° C. or less, and the mixture was stirred for one hour at the same temperature.

After 1N-HCl 200 ml was added dropwise to the reaction solution, the mixture was extracted with heptane 200 ml. The resulting organic layer was washed three times with dil. NaHCO$_3$ and three times with water, and dried over anhydrous magnesium sulfate. The solvent was distilled off under reduced pressure, the residue was purified by silica-gel column chromatography (eluent:heptane), and the solvent was distilled off to obtain yellow oil. The oil was recrystallized from ethanol to obtain 4'-propyl-3,5-difluoro-4-iodobiphenyl 41.5 g. (Yield: 67.4%)

(Step 2) Preparation of 4'-propyl-2',6'-difluoro-3-fluoro-4-trifluoromethoxyterphenyl A mixture of 4'-propyl-3,5-difluoro-4-iodobiphenyl 4.0 g (11.2 mmol) which was obtained at the above step, dihydroxy(3-fluoro-4-trifluoromethoxyphenyl)borane 3.0 g (14.5 mmol), K$_2$CO$_3$ 3.1 g (22.3 mmol), 5% Pd-C ) 0.4 g, and mixed solvent 30 ml of toluene/ethanol/water (1/1/1) was heated to reflux for 10 hours. Then, after Pd-C was filtered off, the mixture was extracted with toluene 100 ml, and the resulting organic layer was washed with water three times and dried over anhydrous magnesium sulfate. The solvent was distilled off under reduced pressure, and the resulting residue was purified by silica-gel column chromatography (eluent: heptane) to obtain crude 4'-propyl-2',6'-difluror-3-fluror-4-trifluoromethoxyterphenyl 4.0 g. The compound was recrystallized from a mixed solvent of ethanol/ethyl acetate (9/1) to obtain the title compound 2.1 g. (Yield: 47.1%)

The compound shows a liquid crystal phase and the transition temperature was C 61.3–61.6 S$_A$ 80.4–80.6 Iso.

The structure was supported well by the spectral data.

Mass spectrum analysis: 410 (M$^+$)

$^1$H-NMR (CDCl$_3$, TMS internal standard) δ (ppm) 0.97 (t, 3H) 1.52–1.81 (m, 2H) 2.65 (t, 2H) 7.18–7.56 (m, 9H)

In the following, the examples using the compounds of the present invention as components of the liquid crystal compositions will be described. In each using example, NI represents nematic phase-isotropic phase transition temperature (° C.), Δε represents the value of dielectric anisotropy, Δn represents the value of optical anisotropy, η represents viscosity (mPa·s) and Vth represents threshold voltage (V).

Further, η was measured at 20° C., and Δε, Δn and Vth were measured at 25° C., respectively.

EXAMPLE 2

Using Example 1

The liquid crystal composition (A) comprising the following cyanophenylcyclohexane type liquid crystal compounds:

| | |
|---|---|
| 4-(trans-4-propylcyclohexyl)benzonitrile | 24% |
| 4-(trans-4-pentylcyclohexyl)benzonitrile | 36% |
| 4-(trans-4-heptylcyclohexyl)benzonitrile | 25% |
| 4-(trans-4-pentylcyclohexyl)-4'-cyanobiphenyl | 15% | has the following values of physical properties.

NI:71.7, Δε: 11.0, Δn:0.137, η:26.7, Vth:1.78.

The values of physical properties of liquid crystal composition (B) comprising of this composition (A) 85% and 4'-propyl-2',6'-difluoro-3-fluoro-4-trifluoro (compound No. 1) obtained in Example 1 15% are shown as follows.

Δε:12.9, Δn:0.144, η:31.3, Vth:1.51.

Although this liquid crystal composition (B) was left in a freezer at −20° C., the appearance of a smectic phase and the deposition of crystals were not observed after 60 days.

EXAMPLE 3

Using Example 2

Using the same method as described in Example 1, the following compound can be synthesized. Moreover, the values of physical properties were measured by using the same method as in Example 2.

Compound No.2: 5-B(F,F)BB(F,F)—F
Compound No.3: 2-B(F,F)BB(F,F)—OCF$_3$
Compound No.4: 4-B(F,F)BB(F)—OCF$_3$
Compound No.5: 1-B(F,F)BB—OCF$_3$
Compound No.6: 10-B(F,F)BB(F,F)—OCF$_2$H
Compound No.7: 3-B(F,F)BB(F)—OCF$_2$H
Compound No.8: 6-B(F,F)BB—OCF$_2$H
Compound No.9: 5-B(F,F)BB(F,F)—CF$_3$
Compound No.10: 4O-B(F,F)BB—CF$_3$
Compound No.11: 7-B(F,F)BB(F,F)—CF$_2$H
Compound No.12: 3O1-B(F,F)BB—CF$_2$H
Compound No.13: 2O-B(F,F)BB(F)—CFH$_2$
Compound No.14: 3-B(F)B(F)B(F,F)—F
Δε: 11.9, Δn: 0.140, η:27.1
Compound No.15: 4-B(F)B(F)B(F)—F
Compound No.16: 5-B(F)B(F)B(F,F)—OCF$_3$
Compound No.17: 6-B(F)B(F)B(F)—OCF$_3$
Compound No.18: 3-B(F)B(F)B(F,F)—OCF$_2$H
Δε: 13.3, Δn: 0.140, η: 30.1
Compound No.19: 1-B(F)B(F)B(F)—OCF$_2$H
Compound No.20: 2-B(F)B(F)B—OCF$_2$H
Compound No.21: 5-B(F)B(F)B(F,F)—CF$_3$
Compound No.22: 3-B(F)B(F)B(F,F)—CF$_2$H
Compound No.23: 7-B(F)B(F)B(F)—CF$_2$H
Compound No.24: 12-B(F)B(F)B—CF$_2$H
Compound No.25: 1O$_3$O—B(F)B(F)B(F,F)—CFH$_2$
Compound No.26: 3-BB(F,F)B(F,F)—F
Δε: 13.4, Δn: 0.141, η: 34.3
Compound No.27: 3-BB(F,F)B(F,F)—OCF$_3$
Δε: 13.5, Δn: 0.141, η: 34.0
Compound No.28: 3-BB(F,F)B(F)—OCF$_3$
Δε: 13.5, Δn: 0.142, η: 34.0
Compound No.29: 3-BB(F,F)B(F,F)—OCF$_2$H
Compound No.30: 5-BB(F,F)B(F)—OCF$_2$H
Compound No.31: 7-BB(F,F)B—OCF$_2$H
Compound No.32: 9-BB(F,F)B(F,F)—CF$_3$
Compound No.33: 3-BB(F,F)B(F)—CF$_3$
Δε: 13.5, Δn: 0.142, η: 34.0
Compound No.34: 2-BB(F,F)B(F,F)—CFH$_2$
Compound No.35: 4-BB(F,F)B(F)—CF$_2$H
Compound No.36: 6-BB(F,F)B—CF$_2$H
Compound No.37: 1O5-BB(F,F)B(F)—CFH$_2$
Compound No.38: 3-B(F,F)B(F)B(F,F)—F
Compound No.39: 5-B(F,F)B(F)B(F)—F
Compound No.41: 3-B(F,F)B(F)B(F,F)—CL
Compound No.42: 5-B(F,F)B(F)B(F,F)—OCF$_3$
Compound No.43: 4-B(F,F)B(F)B(F)—OCF$_3$
Compound No.44: 12O1-B(F,F)B(F)B—OCF$_3$
Compound No.45: 2-B(F,F)B(F)B(F,F)—OCF$_2$H
Compound No.46: 3-B(F,F)B(F)B(F)—OCF$_2$H
Compound No.47: 6-B(F,F)B(F)B—OCF$_2$H
Compound No.48: 10-B(F,F)B(F)B(F,F)—CF$_3$
Compound No.49: 3-B(F,F)B(F)B(F)—CF$_3$
Δε: 14.1, Δn: 0.137, η: 30.9
Compound No.50: 5O1O-B(F,F)B(F)B(F,F)—CF$_2$H
Compound No.51: 7O-B(F,F)B(F)B(F)—CF$_2$H
Compound No.52: 4-B(F,F)B(F)B(F,F)—CFH$_2$
Compound No.53: 5-B(F)B(F,F)B(F,F)—F
Compound No.54: 3-B(F)B(F,F)B(F)—F Δε: 12.8, Δn: 0.141, η: 29.3
Compound No.55: 4-B(F)B(F,F)B—F
Compound No.56: 6-B(F)B(F,F)B(F,F)—CL
Compound No.57: 3-B(F)B(F,F)B(F)—CL
Δε: 13.3, Δn: 0.148, η: 33.4
Compound No.58: 14-B(F)B(F,F)B—CL
Compound No.59: 2-B(F)B(F,F)B(F,F)—OCF$_3$
Compound No.60: 6-B(F)B(F,F)B(F)—OCF$_3$
Compound No.61: 1O-B(F)B(F,F)B—OCF$_3$
Compound No.62: 7-B(F)B(F,F)B(F,F)—OCF$_2$H
Compound No.63: 3-B(F)B(F,F)B(F)—OCF$_2$H
Compound No.64: 3-B(F)B(F,F)B—OCF$_2$H
Compound No.65: 5-B(F)B(F,F)B(F,F)—CF$_3$
Compound No.66: 9-B(F)B(F,F)B(F)—CF$_3$
Compound No.67: 2O2-B(F)B(F,F)B—CF$_3$
Compound No.68: 4-B(F)B(F,F)B(F,F)—CF$_2$H
Compound No.69: 5-B(F)B(F,F)B(F)—CF$_2$H
Compound No.70: 5-B(F)B(F,F)B—CF$_2$H
Compound No.71: 3-B(F)B(F,F)B(F)—CFH$_2$
Compound No.72: 4-B(F,F)B(F,F)B(F,F)—F
Compound No.73: 5-B(F,F)B(F,F)B(F)—F
Compound No.74: 5O-B(F,F)B(F,F)B—F
Compound No.75: 3-B(F,F)B(F,F)B(F,F)—CL
Compound No.76: 5-B(F,F)B(F,F)B(F)—CL
Compound No.77: 3-B(F,F)B(F,F)B (F,F)—OCF$_3$
Δε: 15.3, Δn: 0.140, η: 31.8
Compound No.78: 1-B(F,F)B(F,F)B(F)—OCF$_3$
Compound No.79: 2-B(F,F)B(F,F)B(F,F)-OCF$_2$H
Compound No.80: 3-B(F,F)B(F,F)B(F)—OCF$_2$H
Compound No.81: 4-B(F,F)B(F,F)B—OCF$_2$H
Compound No.82: 5-B(F,F)B(F,F)B(F,F)—CF$_3$
Compound No.83: 6-B(F,F)B(F,F)B(F)—CF$_3$
Compound No.84: 7-B(F,F)B(F,F)B—CF$_3$
Compound No.85: 2-B(F,F)B(F,F)B(F,F)—CF$_2$H
Compound No.86: 3-B(F,F)B(F,F)B(F)—CF$_2$H
Compound No.87: 5-B(F,F)B(F,F)B—CF$_2$H
Compound No.88: 1O3-B(F,F)B(F,F)B(F,F)—CF$_2$H

EXAMPLE 4

Using Example 3

The values of physical properties of liquid crystal compositions of the above composition example 1 were as follows:

NI:83.8, Δε:10.5, Δn:0.159, η:23.9, Vth:1.48.

Although the liquid crystal composition was left in a freezer at −20° C., the appearance of a smectic phase and the deposition of crystals did not occur after 60 days.

EXAMPLE 5

Using Example 4

The values of physical properties of liquid crystal compositions of the above composition example 2 were as follows:

NI:86.3, Δε:9.7, Δn:0.163, η:23.1, Vth:1.85.

Although the liquid crystal composition was left in a freezer at −20° C., the appearance of a smectic phase and the deposition of crystals did not occur after 60 days.

EXAMPLE 6

Using Example 5

The values of physical properties of liquid crystal compositions of the above composition example 3 were as follows:

NI:93.3, Δε:30.3, Δn:0.152, η:87.2, Vth:0.95.

Although the liquid crystal composition was left in a freezer at −20° C., the appearance of the smectic phase and the deposition of crystals did not occur after 60 days.

EXAMPLE 7

Using Example 6

The values of physical properties of liquid crystal compositions of the above composition example 4 were as follows:

NI:83.6, Δε:7.1, Δn:0.199, η:37.4, Vth:2.12.

Although the liquid crystal composition was left in a freezer at −20° C., the appearance of a smectic phase and the deposition of crystals did not occur after 60 days.

EXAMPLE 8

Using Example 7

The values of physical properties of liquid crystal compositions of the above composition example 5 were as follows:

NI:66.6, Δε:11.5, Δn:0.132, η:40.3, Vth:1.30.

Although the liquid crystal composition was left in a freezer at −20° C., the appearance of a smectic phase and the deposition of crystals did not occur after 60 days.

EXAMPLE 9

Using Example 8

The values of physical properties of liquid crystal compositions of the above composition example 6 were as follows:

NI:74.3, Δε:10.3, Δn:0.144, η:24.4, Vth:1.23.

Although the liquid crystal composition was left in a freezer at −20° C., the appearance of a smectic phase and the deposition of crystals did not occur after 60 days.

EXAMPLE 10

Using Example 9

The values of physical properties of liquid crystal compositions of the above composition example 7 were as follows:

NI:77.5, Δε:22.5, Δn:0.118, η:22.5, Vth:1.17.

Although the liquid crystal composition was left in a freezer at −20° C., the appearance of a smectic phase and the deposition of crystals did not occur after 60 days.

EXAMPLE 11

Using Example 10

The values of physical properties of liquid crystal compositions of the above composition example 8 were as follows:

NI:93.5, Δε:6.2, Δn:0.121, η:18.1, Vth:1.74.

Although the liquid crystal composition was left in a freezer at −20° C., the appearance of a smectic phase and the deposition of crystals did not occur after 60 days.

EXAMPLE 12

Using Example 11

The values of physical properties of liquid crystal compositions of the above composition example 9 were as follows:

NI:83.8, Δε:29.2, Δn:0.140, η:42.7, Vth:0.76.

Although the liquid crystal composition was left in a freezer at −20° C., the appearance of a smectic phase and the deposition of crystals did not occur after 60 days.

EXAMPLE 13

Using Example 12

The values of physical properties of liquid crystal compositions of the above composition example 10 were as follows:

NI:59.4, $\Delta\epsilon$:10.9, $\Delta$n:0.118, $\eta$:28.7, Vth:1.18.

Although the liquid crystal composition was left in a freezer at −20° C., the appearance of a smectic phase and the deposition of crystals did not occur after 60 days.

EXAMPLE 14

Using Example 13

The values of physical properties of liquid crystal compositions of the above composition example 11 were as follows:

NI:67.3, $\Delta\epsilon$:7.5, $\Delta$n:0.160, $\eta$:24.1, Vth:1.52.

Although the liquid crystal composition was left in a freezer at −20° C., the appearance of a smectic phase and the deposition of crystals did not occur after 60 days.

EXAMPLE 15

Using Example 14

The values of physical properties of liquid crystal compositions of the above composition example 12 were as follows:

NI:98.5, $\Delta\epsilon$:6.2, $\Delta$n:0.097, $\eta$:26.6, Vth:2.01.

Although the liquid crystal composition was left in a freezer at −20° C., the appearance of a smectic phase and the deposition of crystals did not occur after 60 days.

EXAMPLE 16

Using Example 15

The values of physical properties of liquid crystal compositions of the above composition example 13 were as follows:

NI:87.1, $\Delta\epsilon$:4.3, $\Delta$n:0.097, $\eta$:19.7, Vth:2.44.

Although the liquid crystal composition was left in a freezer at −20° C., the appearance of a smectic phase and the deposition of crystals did not occur after 60 days.

EXAMPLE 17

Using Example 16

The values of physical properties of liquid crystal compositions of the above composition example 14 were as follows:

NI:75.2, $\Delta\epsilon$:10.5, $\Delta$n:0.128, $\eta$:28.7, Vth:1.29.

Although the liquid crystal composition was left in a freezer at −20° C., the appearance of a smectic phase and the deposition of crystals did not occur after 60 days.

EXAMPLE 18

Using Example 17

The values of physical properties of liquid crystal compositions of the above composition example 15 were as follows:

NI:67.6, $\Delta\epsilon$:10.9, $\Delta$n:0.092, $\eta$:30.2, Vth:1.22.

Although the liquid crystal composition was left in a freezer at −20° C., the appearance of a smectic phase and the deposition of crystals did not occur after 60 days.

EXAMPLE 19

Using Example 18

The values of physical properties of liquid crystal compositions of the above composition example 16 were as follows:

NI:67.4, $\Delta\epsilon$:15.7, $\Delta$n:0.105, $\eta$:37.8, Vth:1.05.

Although the liquid crystal composition was left in a freezer at −20° C., the appearance of a smectic phase and the deposition of crystals did not occur after 60 days.

EXAMPLE 20

Using Example 19

The values of physical properties of liquid crystal compositions of the above composition example 17 were as follows:

NI:86.3, $\Delta\epsilon$:7.4, $\Delta$n:0.138, $\eta$:22.1, Vth:1.92.

Although the liquid crystal composition was left in a freezer at −20° C., the appearance of a smectic phase and the deposition of crystals did not occur after 60 days.

EXAMPLE 21

Using Example 20

The values of physical properties of liquid crystal compositions of the above composition example 18 were as follows:

NI:90.5, $\Delta\epsilon$:12.0, $\Delta$n:0.134, $\eta$:37.7, Vth:1.14.

Although the liquid crystal composition was left in a freezer at −20° C., the appearance of a smectic phase and the deposition of crystals did not occur after 60 days.

EXAMPLE 22

Using Example 21

The values of physical properties of liquid crystal compositions of the above composition example 19 were as follows:

NI:81.4, $\Delta\epsilon$:6.3, $\Delta$n:0.098, $\eta$:16.9, Vth:1.98.

Although the liquid crystal composition was left in a freezer at −20° C., the appearance of a smectic phase and the deposition of crystals did not occur after 60 days.

EXAMPLE 23

Using Example 22

The values of physical properties of liquid crystal compositions of the above composition example 20 were as follows:

NI:63.1, $\Delta\epsilon$:9.9, $\Delta$n:0.096, $\eta$:27.5, Vth:1.34.

Although the liquid crystal composition was left in a freezer at −20° C., the appearance of a smectic phase and the deposition of crystals did not occur after 60 days.

EXAMPLE 24

Using Example 23

The values of physical properties of liquid crystal compositions of the above composition example 8 were as follows:

NI:92.4, $\Delta\epsilon$:8.8, $\Delta$n:0.142, $\eta$:37.4, Vth:1.64.

Although the liquid crystal composition was left in a freezer at −20° C., the appearance of a smectic phase and the deposition of crystals did not occur after 60 days.

INDUSTRIAL APPLICABILITY

The liquid crystalline compounds of the present invention have a very high voltage ratio, a low threshold voltage, very little variation of these properties with temperature, and high Δn, and the compatibility of these compounds with the other liquid crystal materials is improved. Further, new liquid crystalline compounds having necessary physical properties can be provided from the crystalline compounds of the present invention by optional selection of substituted groups.

Accordingly, new liquid crystal compositions having a very high voltage holding ratio, very little variation of this property with temperature, a low threshold voltage, appropriate Δn and Δε, stability, and excellent compatibility with other liquid crystal materials can be provided by using the liquid crystalline compounds of the present invention as components of liquid crystal compositions. Moreover, liquid crystal display devices constituted by using these can be provided.

What is claimed is:

1. A terphenyl derivative represented by formula (1);

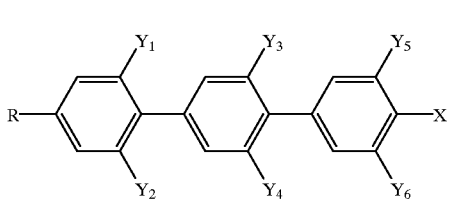

(1)

wherein R represents a straight or branched alkyl group of 1–10 carbon atoms, and any methylene groups (—CH$_2$—) not adjacent each other in each alkyl group may be replaced by an oxygen atom;

X represents F, —OCF$_3$, —OCF$_2$H, —CF$_3$, —CF$_2$H, or CFl—$_2$;

Y$_1$, Y$_2$, Y$_3$, and Y$_4$, Y$_5$ and Y$_6$ independently represent H or F, but at least two of Y$_1$, Y$_2$, Y$_3$ and Y$_4$ represent F, and Y$_5$ and Y$_6$ represent H;

provided that
  a) when Y$_1$=Y$_2$=F and Y$_3$=Y$_4$=H, then X is not F,
  b) when Y$_1$=Y$_3$=F and Y$_2$=Y$_4$=H, then X is not F, —CF$_3$ and —OCF$_3$,
  c) when Y$_3$=Y$_4$=F and Y$_1$=Y$_2$=H, then X is not F, —CF$_3$ and —OCF$_3$,
  d) when Y$_1$=Y$_2$=Y$_3$=F and Y$_2$=H, then X is not F, —CF$_3$ and —CF$_2$H,
  e) when Y$_1$=Y$_2$=Y$_3$=Y$_4$=F, then X is not —OCF$_3$.

2. The terphenyl derivative according to claim 1, wherein Y$_1$=Y$_2$=F, Y$_3$=Y$_4$=H and X=CF$_3$ or —CF$_2$H.

3. The terphenyl derivative according to claim 1 wherein Y$_1$=Y$_2$=F, Y$_3$=Y$_4$=H and X=—OCF$_3$ or —OCF$_2$H.

4. The terphenyl derivative according to claim 1 wherein Y$_1$=Y$_3$=F, Y$_2$=Y$_4$=H, and X=OCF$_2$H or —CF$_2$H.

5. The terphenyl derivative according to claim 1 wherein Y$_3$=Y$_4$=F, Y$_1$=Y$_2$=H, and X=—OCF$_2$H or —CF$_2$H.

6. The terphenyl derivative according to claim 1 wherein Y$_1$=Y$_3$=F, Y$_4$=H, and X=—OCF$_3$ or —OCF$_2$H.

7. The terphenyl derivative according to claim 1 wherein Y$_1$=Y$_3$=Y$_4$=F, and Y$_2$=H.

8. The terphenyl derivative according to claim 1 wherein Y$_1$=Y$_2$=Y$_3$=Y$_4$=F, and X=F, —CF$_3$, —CF$_2$H, or —OCF$_2$H.

9. A liquid crystal composition comprising at least one of the terphenyl derivatives according to claim 1.

10. A liquid crystal composition comprising as a first component thereof at least one derivative selected from the terphenyl derivatives according to claim 1, and as a second component thereof at least one compound selected from the group consisting of the compounds represented by formula (2), (3), or (4)

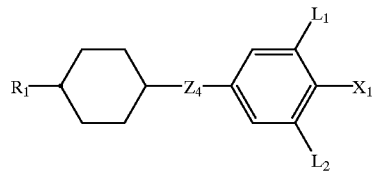

(2)

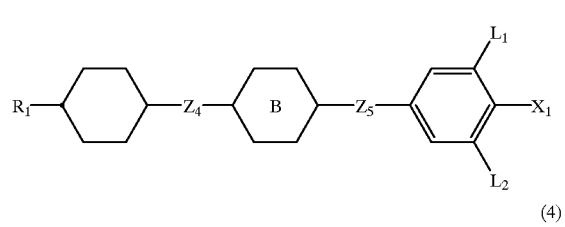

(3)

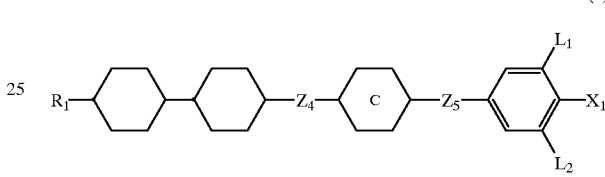

(4)

wherein R, is an alkyl group of 1–10 carbon atoms, any nonadjacent methylene groups in said alkyl group may be substituted by oxygen atoms of —CH═CH—, and any hydrogen atoms in the alkyl group may be substituted by fluorine atoms;

X, is F, Cl, —OCF$_3$, —OCF$_2$H, —CCF$_3$, —CF$_2$H, —CFH$_2$, —OCF$_3$CF$_2$H, or —OCF$_2$CFHCF$_3$;

L$_1$ and L$_2$ independently are H or F;

Z$_4$ and Z$_5$ independently are a 1,2-ethylene group, a 1,4-butylene group, —COO—, —CF$_2$O—, —OCF$_2$—, —CH═CH—, or a covalent bond;

ring B is trans-1,4-cyclohexylene, 1,3-dioxane-2,5-diyl, or 1,4-phenylene where the hydrogen atoms may be substituted by fluorine atoms;

ring C is trans-1,4-cyclohexylene or 1,4-phenylene wherein the hydrogen atoms may be substituted by fluorine atoms.

11. A liquid crystal composition comprising as a first component thereof at least one compound selected from the compounds according to claim 1, and as a second component thereof at least one compound selected from the group consisting of the compounds of formula (5) or (6)

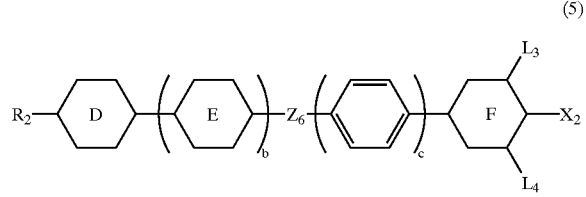

(5)

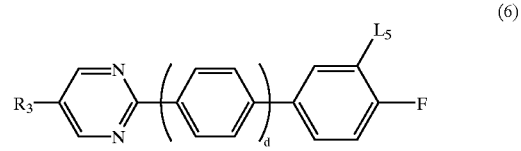

(6)

wherein R$_2$ and R$_3$ independently are an alkyl group of 1–10 carbon atoms, and any nonadjacent methylene groups in said alkyl group may be substituted by oxygen atoms of —CH═CH—, and any hydrogen atoms in the alkyl group may be substituted by fluorine atoms;

$X_2$ is —CN or —C≡C—CN;

ring D is trans-1,4-cyclohexylene, 1,4-phenylene, 1,3-dioxane-2,5-diyl, or pyrimidine-2,5-diyl; trans-1, 4 cyclohexylene, 1,4-phenylene, 1,3dioxane-2,5-diyl, or pyrimidine-2,5-diyl;

ring E is trans-1,4 cyclohexylene, 1,4-phenylene wherein the hydrogen atoms may be substituted by fluorine atoms, or pyrimidine-2,5-diyl;

ring F is trans-1,4-cyclohexylene or 1,4-phenylene;

$Z_6$ is 1,2-ethylene, —COO—, or a covalent bond;

$L_3$, $L_4$ and $L_5$ independently are hydrogen or fluorine;

b, c, and d independently are 0 or 1.

12. A liquid crystal composition comprising as a first component thereof at least one compound selected from the compounds according to claim 1, and as a second component thereof at least one compound selected from the group consisting of compounds represented by formula (2), (3), or (4) as defined in claim 11;

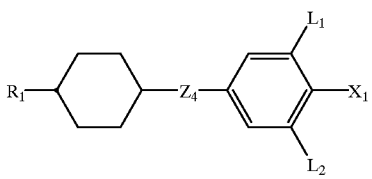
(2)

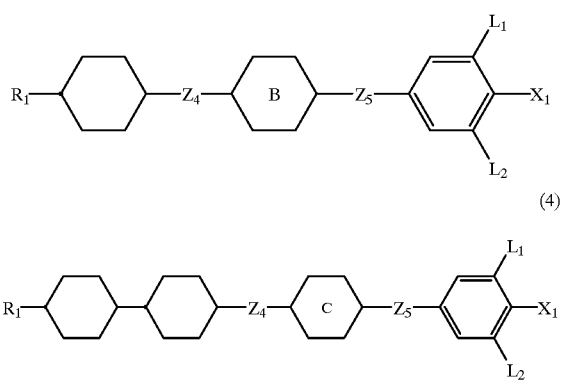
(3)

(4)

wherein $R_1$ is an alkyl group of 1–10 carbon atoms, any nonadjacent methylene groups in said alkyl group may be substituted by oxygen atoms of —CH═CH—, and any hydrogen atoms in the alkyl group may be substituted by fluorine atoms;

$X_1$ is F, Cl, —OCF$_3$, —OCF$_2$H, —CCF$_3$, —CF$_2$H, —CFH$_2$, —OCF$_3$CF$_2$H, or —OCF$_2$CFHCF$_3$;

$L_1$ and $L_2$ independently are H or F;

$Z_4$ and $Z_5$ independently are a 1,2-ethylene group, a 1,4-butylene group, —COO—, —CF$_2$O—, —OCF$_2$—, —CH═CH, or a covalent bond;

ring B is trans-1,4-cyclohexylene, 1,3-dioxane-2,5-diyl, or 1,4-phenylene where the hydrogen atoms may be substituted by fluorine atoms;

ring C is trans-1,4cyclohexylene or 1,4-phenylene wherein the hydrogen atoms may be substituted by fluorine atoms;

and as a third component thereof at least one compound selected from the group consisting of compounds of formula (7), (8), to (9);

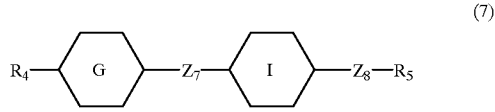
(7)

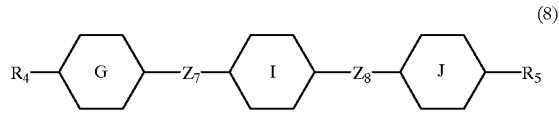
(8)

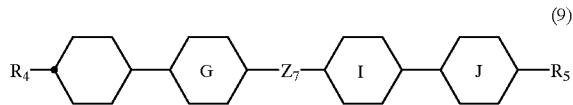
(9)

wherein $R_4$ and $R_5$ independently are an alkyl group of 1–10 carbon atoms, and any nonadjacent methylene groups in said alkyl group may be substituted by oxygen atoms of —CH═CH—, and any hydrogen atoms in said alkyl group may be substituted by fluorine atoms;

ring G, ring J, and ring I independently are trans-1,4-cyclohexylene, pyrimidine-2,5-diyl, or 1,4-phenylene wherein the hydrogen atoms may be substituted by fluorine atoms;

$Z_7$ and $Z_8$ are independently —C≡C—, —COO—, —CH$_2$—CH$_2$—, —CH═CH— or a covalent bond.

13. A liquid crystal composition comprising as a first component thereof at least one compound selected from the compounds according to claim 1;

as a second component thereof at least one compound selected from the group consisting of compounds represented by formula (5) or (6);

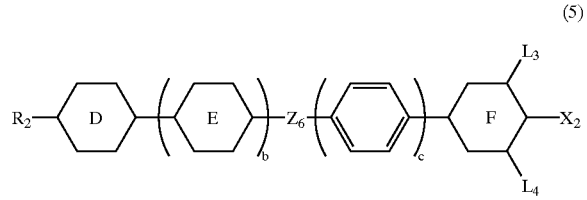
(5)

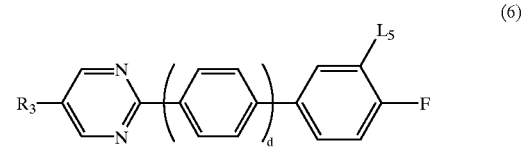
(6)

wherein $R_2$ and $R_3$ independently are an alkyl group of 1–10 carbon atoms, and any nonadjacent methylene groups in said alkyl group may be substituted by oxygen atoms of —CH═CH—, and any hydrogen atoms in the alkyl group may be substituted by fluorine atoms;

$X_2$ is CN—or C≡CN;

ring D is trans-1,4-cyclohexylene, 1,4-phenylene, 1, 3-dioxane-2,5-diyl, or pyrimidine-2,5-diyl; trans-1,4 cyclohexylene, 1,4-phenylene, 1,3-dioxane-2,5-diyl, or pyrimidine-2,5-diyl;

ring E is trans-1,4 cyclohexylene, 1,4-phenylene wherein the hydrogen atoms may be substituted by fluorine atoms, or pyrimidine-2,5-diyl;

ring F is trans-1,4-cyclohexylene or 1,4-phenylene;
$Z_6$ is 1,2-ethylene, —COO—, or a covalent bond;
$L_3$, $L_4$ and $L_5$ independently are hydrogen or fluorine;
b, c, and d independently are 0 or 1 as a third component thereof at least one compound selected from the group consisting of the compounds of formula (7), (8), or (9)

(7)
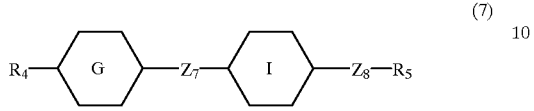

(8)
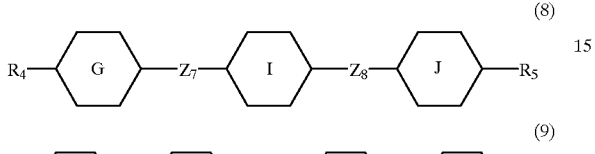

(9)
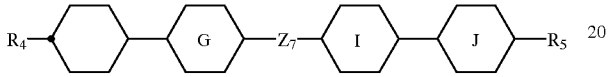

wherein $R_4$ and $R_5$ independently are an alkyl group of 1–10 carbon atoms, and any nonadjacent methylene groups in said alkyl group may be substituted by oxygen atoms of —CH=CH—, and any hydrogen atoms in said alkyl group may be substituted by fluorine atoms;

ring G, ring J, and ring I independently are trans-1,4-cyclohexylene, pyrimidine-2,5-diyl, or 1,4-phenylene wherein the hydrogen atoms may be substituted by fluorine atoms;

$Z_7$ and $Z_8$ are independently —C≡C—, —COO—, —CH$_2$—CH—, —CH=CH— or a covalent bond.

14. A liquid crystal composition comprising as a first component thereof at least one compound selected from the compounds according to claim 1;

as a second component thereof at least one compound selected from the group consisting of the compounds of formula (2), (3), or (4)

(2)
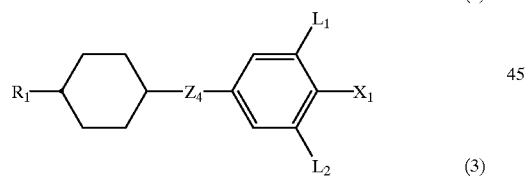

(3)
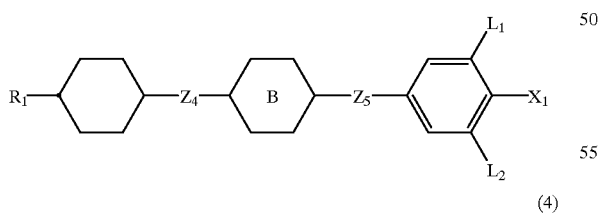

(4)
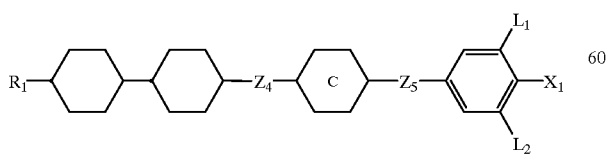

wherein $R_1$ is an alkyl group of 1–10 carbon atoms, any nonadjacent methylene groups in said alkyl group may be substituted by oxygen atoms of —CH=CH—, and any hydrogen atoms in the alkyl group may be substituted by fluorine atoms;

$X_1$ is F, Cl, —OCF$_3$, —OCF$_2$H, —CCF$_3$, —CF$_2$H, —CFH$_2$, —OCF$_3$CF$_4$H, or —OCF$_2$CFHCF$_3$;

$L_1$ and $L_2$ independently are H or F;

$Z_4$ and $Z_5$ independently are a 1,2-ethylene group, a 1,4-butylene group, —COO—, —CF$_2$O—, —OCF$_2$—, —CH=CH, or a covalent bond;

ring B is trans-1,4-cyclohexylene, 1,3-dioxane-2,5-diyl, or 1,4-phenylene where the hydrogen atoms;

ring C is trans-1,4-cyclohexylene or 1,4-phenylene wherein the hydrogen atoms may be substituted by fluorine atoms may be substituted by fluorine atom;

as a third component thereof at least one compound selected from the group consisting of the compounds of formula (5) or (6)

(5)
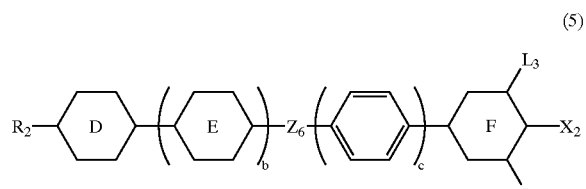

(6)
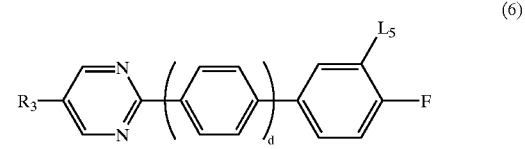

wherein $R_2$ and $RR_3$ independently are an alkyl group of 1–10 carbon atoms, and any nonadjacent methylene groups in said alkyl group may be substituted by oxygen atoms of —CH=CH—, and any hydrogen atoms in the alkyl group may be substituted by fluorine atoms;

$X_2$ is —CN or —C≡CN;

ring D is trans-1,4-cyclohexylene, 1,4-phenylene, 1,3-dioxane-2,5-diyl, or pyrimidine-2,5-diyl; trans-1,4 cyclohexylene, 1,4-phenylene, 1,3- dioxane-2,5-diyl, or pyrimidine-2,5-diyl;

ring E is trans-1,4 cyclohexylene, 1,4-phenylene wherein the hydrogen atoms may be substituted by fluorine atoms, or pyrimidine-2,5-diyl;

ring F is trans-1,4-cyclohexylene or 1,4-phenylene;

$Z_6$ is 1,2-ethylene, —COO—, or a covalent bond;

$L_3$, $L_4$ and $L_5$ independently are hydrogen or fluorine;

b, c, and d independently are 0 or 1;

as a fourth component thereof at least one compound selected from the group consisting of the compounds of formula (7), (8), or (9)

(7)
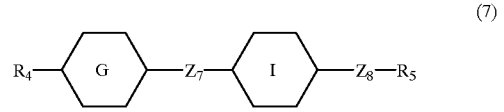

(8)
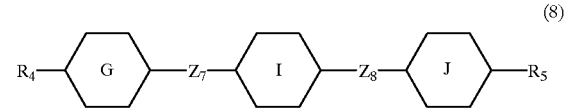

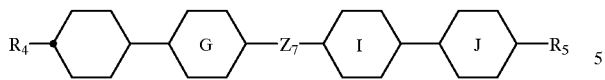

(9)

wherein $R_1$ is an alkyl group of 1–10 carbon atoms, any nonadjacent methylene groups in said alkyl groups may be substituted by oxygen atoms of —CH=CH—, and any hydrogen atoms in the alkyl group may be substituted by fluorine atoms;

$X_1$ is F, Cl, —OCF$_3$, —OCF$_2$H, —CCF$_3$, —CF$_2$H, —CFH$_2$, —OCF$_3$CF$_2$H, or —OCF$_2$CFHCF$_3$;

$L_1$ and $L_2$ independently are H or F;

$Z_4$ and $Z_5$ independently are a 1,2-ethylene group, a 1,4-butylene group, —COO—, —CF$_2$O—, —OCF$_2$—, —CH=CH, or a covalent bond;

ring B is trans-1,4-cyclohexylene, 1,3-dioxane-2,5-diyl, or 1,4-phenylene where the hydrogen atoms may be substituted by fluorine atoms;

ring C is trans-1,4-cyclohexylene or 1,4-phenylene wherein the hydrogen atoms may be substituted by fluorine atoms.

15. A liquid crystal; composition comprising the liquid crystal composition according to claim 10 and at least one optically active compound.

16. A liquid crystal display device made using the liquid crystal composition according to claim 15.

* * * * *